(12) United States Patent
Weber et al.

(10) Patent No.: US 7,691,611 B2
(45) Date of Patent: Apr. 6, 2010

(54) PRODUCTION OF RECOMBINANT IL-18 BINDING PROTEIN

(75) Inventors: Urs Weber, La Tour-de-Peilz (CH); Thierry Ziegler, Leognan (FR)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 11/915,453

(22) PCT Filed: Jun. 1, 2006

(86) PCT No.: PCT/EP2006/062851

§ 371 (c)(1),
(2), (4) Date: Nov. 26, 2007

(87) PCT Pub. No.: WO2006/128908

PCT Pub. Date: Dec. 7, 2006

(65) Prior Publication Data

US 2008/0199913 A1    Aug. 21, 2008

Related U.S. Application Data

(60) Provisional application No. 60/687,631, filed on Jun. 3, 2005.

(30) Foreign Application Priority Data

Jun. 3, 2005  (EP)  ................................. 05104878
Jul. 13, 2005 (EP)  ................................. 05106429

(51) Int. Cl.
C12P 21/04   (2006.01)
C07K 14/00   (2006.01)

(52) U.S. Cl. ...................................... 435/70.1; 530/350

(58) Field of Classification Search ........................ None
See application file for complete search history.

(56) References Cited

U.S. PATENT DOCUMENTS

| 2007/0037734 A1 | 2/2007 | Rossi et al. |
| 2007/0134761 A1 | 6/2007 | Chatellard et al. |
| 2007/0196895 A1 | 8/2007 | Aloni et al. |
| 2007/0258962 A1 | 11/2007 | Chatellard et al. |
| 2007/0293658 A1 | 12/2007 | Kornmann et al. |
| 2008/0076708 A1 | 3/2008 | Altarocca et al. |

FOREIGN PATENT DOCUMENTS

| WO | WO 99/09063     |   | 2/1999 |
| WO | WO 9909063 A1   | * | 2/1999 |
| WO | WO 01/18175     |   | 3/2001 |
| WO | WO 0118175 A1   | * | 3/2001 |
| WO | WO 2004/081167 A2 |  | 9/2004 |
| WO | WO 2004/101617 A1 |  | 11/2004 |

(Continued)

OTHER PUBLICATIONS

Meuwly et al., (Cytotechnology. Sep. 2004;46(1):37-47).*

(Continued)

*Primary Examiner*—Cherie M Woodward
(74) *Attorney, Agent, or Firm*—Saliwanchik, Lloyd & Saliwanchik

(57) ABSTRACT

The invention relates to a process for the production of IL-18 binding protein (IL-18BP), and to a composition comprising IL-18BP characterized by a specific glycosylation pattern.

22 Claims, 14 Drawing Sheets

FOREIGN PATENT DOCUMENTS

| WO | WO 2005/040384 A1 | 5/2005 |
|---|---|---|
| WO | WO 2005/049649 A1 | 6/2005 |
| WO | WO 2005/083058 A1 | 9/2005 |
| WO | WO 2006/003134 A1 | 1/2006 |
| WO | WO 2006/131550 A1 | 12/2006 |

OTHER PUBLICATIONS

IUPAC Compendium of Chemical Terminology, 2nd Edition (1997)—"Bioreactor" definition (1 page).*

Yoon et al., (Biotechnol Bioeng. Feb. 5, 2005;89(3):345-56; epub Dec. 24, 2004).*

Tans et al., (New Developments and Applications in Animal Cell Technology—Part 7. "Development of Proteinase Assays for Improved CHO cell cultures." Springer, Netherlands. pp. 309-316, Abstract Only (2002)) (1 page).*

Ducommun et al., (Biotechnol Bioeng. Mar. 30, 2002;77(7):838-42) (cited on Applicant's IDS of Nov. 26, 2007).*

Goldman et al., (Biotechnol Bioeng. Dec. 5, 1998;60(5):596-607. Feb. 5, 2005;89(3):345-56) (cited on Applicant's IDS of Nov. 26, 2007).*

Pending claims in U.S. Appl. No. 11/916,087, filed Nov. 30, 2007, not yet published.

Altschul, S. F. et al. "Basic Local Alignment Search Tool" *Journal of Molecular Biology*, 1990, pp. 403-410, vol. 215.

Altschul, S. F. et al. "Gapped Blast and PSI-Blast: a new generation of protein database search programs" *Nucleic Acids Research*, 1997, pp. 3389-3402, vol. 25, No. 17.

Anderson, D. C. et al. "Multiple Cell Culture Factors Can Affect the Glycosylation of Asn-184 in CHO-Produced Tissue-Type Plasminogen Activator" *Biotechnology and Bioengineering*, Oct. 5, 2000, pp. 25-31, vol. 70, No. 1.

Chuppa, S. et al. "Fermentor Temperature as a Tool for Control of High-Density Perfusion Cultures of Mammalian Cells" *Biotechnology and Bioengineering*, Jul. 20, 1997, pp. 328-338, vol. 55, No. 2.

Devereux, J. et al. "A comprehensive set of sequence analysis programs for the VAX" *Nucleic Acids Research*, 1984, pp. 387-395, vol. 12, No. 1.

Dowd, J. E. et al. "Glucose-Based Optimization of CHO-Cell Perfusion Cultures" *Biotechnology and Bioengineering*, Oct. 20, 2001, pp. 252-256, vol. 75, No. 2.

Ducommun, P. et al. "On-Line Determination of Animal Cell Concentration in Two Industrial High-Density Culture Processes by Dielectric Spectroscopy" *Biotechnology and Bioengineering*, Feb. 5, 2002, pp. 316-323, vol. 77, No. 3.

Ducommun, P. et al. "Monitoring of Temperature Effects on Animal Cell Metabolism in a Packed Bed Process" *Biotechnology and Bioengineering*, Mar. 30, 2002, pp. 838-842, vol. 77, No. 7.

Gervais, A. et al. "Glycosylation of human recombinant gonadotrophins: characterization and batch-to-batch consistency" *Glycobiology*, 2003, pp. 179-189, vol. 13, No. 3.

Goldman, M. H. et al. "Monitoring Recombinant Human Interferon-Gamma N-Glycosylation During Perfused Fluidized-Bed and Stirred-Tank Batch Culture of CHO Cells" *Biotechnology and Bioengineering*, Dec. 5, 1998, pp. 596-607, vol. 60, No. 5.

Goochee, C. F. et al. "Environmental Effects on Protein Glycosylation" *Biotechnology*, May 1990, pp. 421-427, vol. 8.

Goochee, C. F. et al. "The Oligosaccharides of Glycoproteins: Bioprocess Factors Affecting Oligosaccharide Structure and Their Effect on Glycoprotein Properties" *Biotechnology*, Dec. 1991, pp. 1347-1355, vol. 9.

Grantham, R. "Amino Acid Difference Formula to Help Explain Protein Evolution" *Science*, Sep. 6, 1974, pp. 862-864, vol. 185, No. 4154.

Harvey, D. J. "Identification of protein-bound carbohydrates by mass spectrometry" *Proteomics*, 2001, pp. 311-328, vol. 1.

Hayter, P. M. et al. "The Effect of the Dilution Rate on CHO Cell Physiology and Recombinant Interferon-γ Production in Glucose-Limited Chemostat Culture" *Biotechnology and Bioengineering*, Nov. 5, 1993, pp. 1077-1085, vol. 42, No. 9.

Hermentin, P. et al. "The hypothetical N-glycan charge: a number that characterizes protein glycosylation" *Glycobiology*, 1996, pp. 217-230, vol. 6, No. 2.

Hooker, A. D. et al. "N-Glycans of Recombinant Human Interferon-γ Change During Batch Culture of Chinese Hamster Ovary Cells" *Biotechnology and Bioengineering*, Dec. 20, 1995, pp. 639-648, vol. 48, No. 6.

Hu, W.-S. et al. "Large-scale mammalian cell culture" *Current Opinion in Biotechnology*, 1997, pp. 148-153, vol. 8.

Jenkins, N. L. et al. "Getting the glycosylation right: Implications for the biotechnology industry" *Nature Biotechnology*, Aug. 1996, pp. 975-981, vol. 14.

Kadouri, A. et al. "Some myths and messages concerning the batch and continuous culture of animal cells" *Cytotechnology*, 1997, pp. 89-98, vol. 24.

Kim, S.-H. et al. "Structural requirements of six naturally occurring isoforms of the IL-18 binding protein to inhibit IL-18" *PNAS*, Feb. 1, 2000, pp. 1190-1195, vol. 97, No. 3.

Kyung, Y.-S. et al. "High density culture of mammalian cells with dynamic perfusion based on on-line oxygen uptake rate measurements" *Cytotechnology*, 1994, pp. 183-190, vol. 14.

Novick, D. et al. "Interleukin-18 Binding Protein: A Novel Modulator of the Th1 Cytokine Response" *Immunity*, Jan. 1999, pp. 127-136, vol. 10.

Oh, D. J. et al. "High-Density Continuous Cultures of Hybridoma Cells in a Depth Filter Perfusion System" *Biotechnology and Bioengineering*, Oct. 1994, pp. 895-901, vol. 44, No. 8.

Pearson, W. R. "Rapid and Sensitive Sequence Comparison with FASTP and FASTA" *Methods in Enzymology*, 1990, pp. 63-98, vol. 183.

Puren, A. J. et al. "Gene expression, synthesis, and secretion of interleukin 18 and interleukin 1β are differentially regulated in human blood mononuclear cells and mouse spleen cells" *PNAS*, Mar. 1999, pp. 2256-2261, vol. 96.

Racher, A. J. et al. "Investigation of parameters affecting a fixed bed bioreactor process for recombinant cell lines" *Cytotechnology*, 1993, pp. 125-131, vol. 13.

Racher, A. J. et al. "Influence of ammonium ion and glucose on mAb production in suspension and fixed bed hybridoma cultures" *Journal of Biotechnology*, 1993, pp. 145-156, vol. 29.

Sugiura, T. et al. "Dynamics of recombinant protein production by mammalian cells in immobilized perfusion culture" *Enzyme and Microbial Technology*, 1998, pp. 699-704, vol. 22.

Urushihara, N. et al. "Elevation of Serum Interleukin-18 Levels and Activation of Kupffer Cells in Biliary Atresia" *Journal of Pediatric Surgery*, Mar. 2000, pp. 446-449, vol. 35, No. 3.

Vigers, G. P. A. et al. "Crystal structure of the type-I interleukin-1 receptor complexed with interleukin-1β" *Nature*, Mar. 13, 1997, pp. 190-194, vol. 386.

Wang, M-D. et al. "Erythropoietin Production from CHO Cells Grown by Continuous Culture in a Fluidized-Bed Bioreactor" *Biotechnology and Bioengineering*, Jan. 20, 2002, pp. 194-203, vol. 77, No. 2.

* cited by examiner

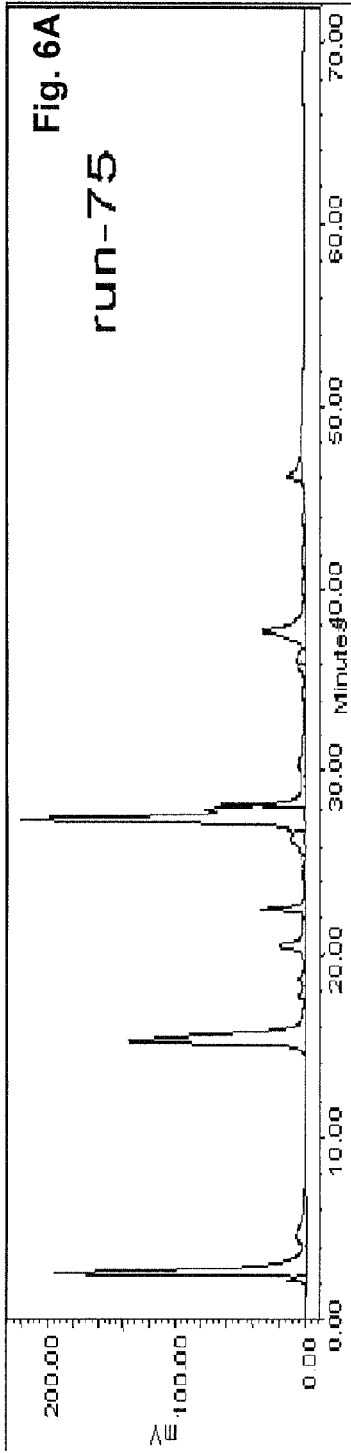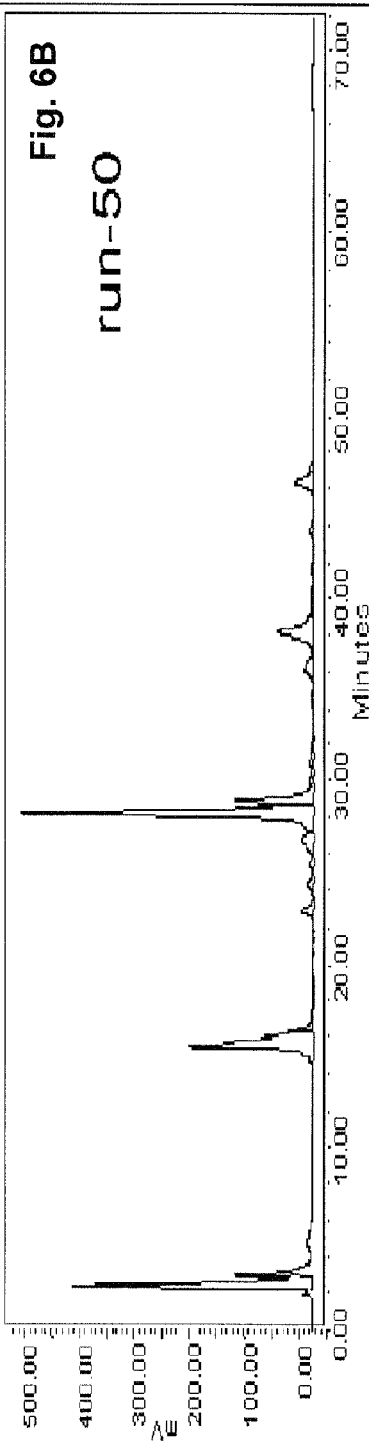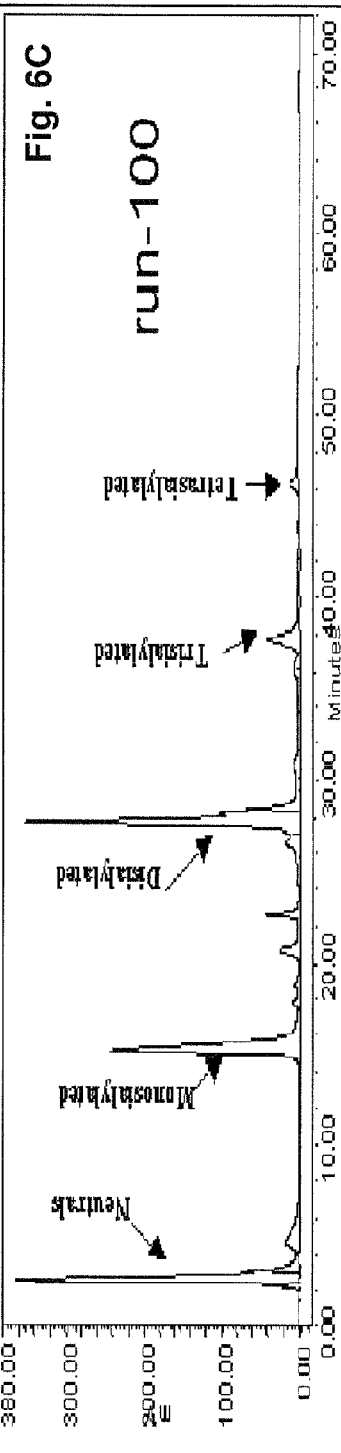

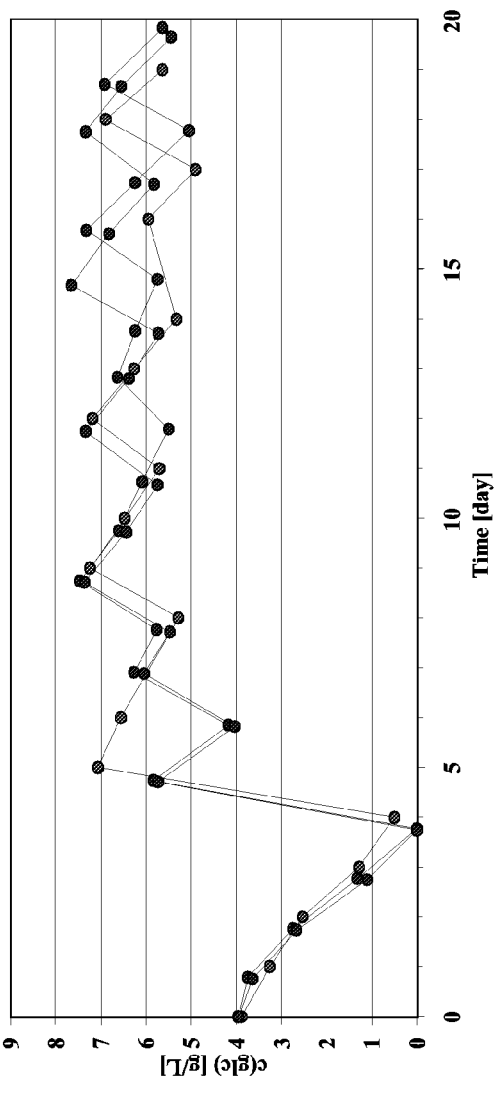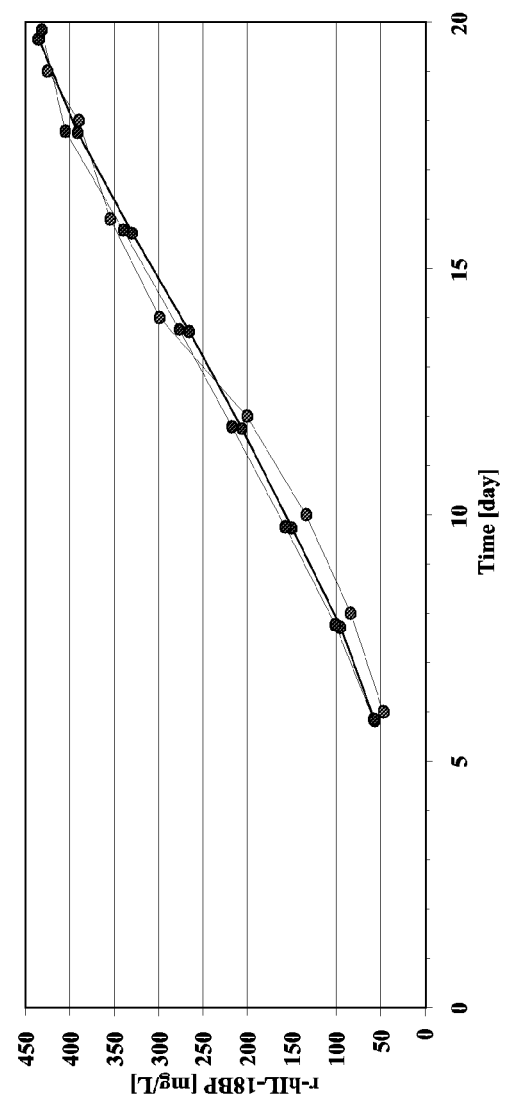
Fig. 7 con'd

PRODUCTION OF RECOMBINANT IL-18 BINDING PROTEIN

CROSS-REFERENCE TO RELATED APPLICATION

This application is the U.S. national stage application of International Patent Application No. PCT/EP2006/062851, filed Jun. 1, 2006, which claims the benefit of U.S. Provisional Patent Application No. 60/687,631, filed Jun. 3, 2005, the disclosures of which are hereby incorporated by reference in their entireties, including all figures, tables and amino acid or nucleic acid sequences.

FIELD OF THE INVENTION

The present invention is in the field of protein production. More specifically, it relates to a process for the production of recombinant IL-18 binding protein (IL-18BP). The invention further relates to an IL-18BP composition characterized by a specific glycosylation profile.

BACKGROUND OF THE INVENTION

Proteins have become commercially important as drugs that are also generally called "biologicals". One of the greatest challenges is the development of cost effective and efficient processes for the production of recombinant proteins on a commercial scale.

The biotech industry makes an extensive use of mammalian cells for the manufacturing of recombinant glycoproteins for human therapy.

Today, fed-batch and perfusion cultures are the two dominant modes of industrial operation for the mammalian cell culture processes that require large amount of proteins (Hu and Aunins 1997). Whatever the production technology of choice is, development efforts aim at obtaining production processes that warrant high volumetric productivity, batch-to-batch consistency, homogenous product quality at low costs.

The decision between fed-batch or perfusion production mode is mainly dictated by the biology of the clone and the property of the product, and is done on a case-by-case basis during the course of the development of a new drug product (Kadouri and Spier 1997).

When the selection is a perfusion process, one of the culture systems of choice is stationary packed-bed bioreactor in which cells are immobilized onto solid carriers. This system is easy to operate and with appropriate carriers and culture conditions very high cell density (of $\sim 10^7 - 10^8$ cell·ml$^{-1}$) can be achieved.

A consequence of this high cell density is the need for an intensive medium perfusion rate (feed and harvest) that should be used in order to keep the cells viable and productive. It appears that the perfusion rate is one of the central parameters of such a process: it drives the volumetric protein productivity, the protein product quality and has a very strong impact on the overall economics of the process.

Therefore at industrial scale the optimal stationary packed-bed bioreactor process should operate with a perfusion rate as low as possible without compromising on quantity and quality of the product.

In the course of reducing the perfusion rate, several studies were conducted where the concentration of glucose (Wang et al. 2002) (Dowd et al. 2001) is used as an indicator of other nutrients level in the feed medium in order to operate the bioreactor at a low perfusion rate without accumulating in the culture high levels of toxic by-products such as lactate and ammonia (Sugiura and Kakuzaki 1998) (Racher et al. 1993). Modification of culture parameters such as pH or temperature (Chuppa et al. 1997) is also a common strategy to optimize culture conditions and reduce medium perfusion needs.

In order to achieve optimal medium perfusion rate, three approaches can be considered:

a) To fix perfusion rate at a constant value during the entire production run.

This approach is usually preferred in industrial production processes, since it is simpler to operate in a robust and consistent way. It also it has the advantage to define medium costs of the process as there is no variation in perfusion rate from run to run.

b) To adjust perfusion rate in response to cell number and/or nutrient consumption such as glucose (Oh et al. 1994) (Dowd et al. 2001) (Gorenflo et al. 2003), glutamine (Gorenflo et al. 2002), or oxygen (Kyung et al. 1994). Although this approach provides a more scientific rationale for adjusting the perfusion rate, it may lead to an overgrown culture and an "out-of-control" increase of the perfusion rate. When cells are cultured in suspension mode, a "culture bleed" is done to avoid overgrowing the culture, but this is not possible when cells are immobilized on a carrier. So in general, this approach is not preferred for manufacturing operations as it is difficult to operate in a robust and consistent manner and the medium perfusion rate needs to be readjusted on a daily basis.

c) To combine both strategies a) and b) with an initial cell propagation phase (or "growth phase") where the perfusion rate is progressively increased according to cell growth requirements during the growth phase followed by a shift of culture conditions such as temperature and/or pH in order to stabilize and keep cell metabolism at a relatively low and constant level. At this stage, the perfusion rate can be reduced to a fixed value, matching the reduced need of the cells throughout the production phase.

It is known that modification of the perfusion rate during a perfusion process, as well as modification of other bioprocess factors, can influence the recombinant protein quality and in particular its glycosylation pattern (Jenkins et al. 1996) (Andersen et al. 2000). Glycosylation is usually recognized as an important function in the solubility, immunogenicity, and pharmacokinetic properties of human glycoproteins and those are key parameters in the safety and clinical efficacy of a product (Goochee et al. 1991). In particular, glycosylation affects folding and secretion of many glycoproteins, as well as their plasma half-life, thus having an important impact on in vivo biology and activity of glycosylated proteins.

In general, the term "glycosylation" of a protein refers to the formation of the sugar-amino acid linkage. Glycosylation is a crucial event in the biosynthesis of the carbohydrate units of (secreted) glycoproteins. It sets into motion a complex series of posttranslational enzymatic steps that lead to the formation of a host of protein-bound oligosaccharides with diverse biological functions.

Mammalian glycoproteins commonly contain three types of constituent glycans; the N-linked glycans which are attached to asparagine via an N-acetylglucosamine (GlcNAc) residue in an Asn-Xxx-(Ser, Thr) motif, where Xxx can be any amino acid except proline, those attached to serine or threonine, referred to as O-linked glycans and the carbohydrate components of glycosylphosphatidylinositol. Although many variations are possible, the antennae of mature glycans usually consist of one or more N-acetyllactosamine units with the chains terminating in either sialic acid or α-linked galactose. Fucose is frequently found attached to the asparagine-linked GlcNAc residue and often, additionally on the antennae. Other common modifications to the basic structure include a GlcNAc residue attached to the 4-position of the core branching mannose residue, referred to as a "bisecting" GlcNAc residue and sulphate groups which can be found in a variety of locations, both on the core and the antennae.

The biosynthesis of these compounds involves attachment to the asparagine of a glycan containing the trimannosyl-chitobiose core together with an additional six mannose and three glucose residues followed by removal of the glucose and four mannose residues. Various other glycosyl transferases and glycosidases then process the (GlcNAc)2(Man)5 structure to the mature glycan. This process results in three general types of N-linked glycan depending on the extent of processing; "high-mannose" glycans in which only mannose resides on the two antennae, "hybrid glycans" in which one antenna is processed and "complex" glycans where both antennae are modified. O-linked glycans, on the other hand, are much more diverse, ranging from monosaccharides to large sulphated polysaccharides with no common core structure or consensus sequence of amino acids at the attachment site (Harvey, 2001).

One such glycosylated protein of therapeutic interest is interleukin-18 binding protein.

Interleukin-18 binding protein (IL-18BP) is a naturally occurring soluble protein that was initially affinity purified, on an IL-18 column, from urine (Novick et al. 1999). IL-18BP abolishes IL-18 induction of IFN-γ and IL-18 activation of NF-κB in vitro. In addition, IL-18BP inhibits induction of IFN-γ in mice injected with LPS.

The IL-18BP gene was localized to the human chromosome 11, and no exon coding for a transmembrane domain could be found in the 8.3 kb genomic sequence comprising the IL-18BP gene. Four isoforms of IL-18BP generated by alternative mRNA splicing have been identified in humans so far. They were designated IL-18BP a, b, c, and d, all sharing the same N-terminus and differing in the C-terminus (Novick et al 1999). These isoforms vary in their ability to bind IL-18 (Kim et al. 2000). Of the four human IL-18BP (hIL-18BP) isoforms, isoforms a and c are known to have a neutralizing capacity for IL-18. The most abundant IL-18BP isoform, isoform a, exhibits a high affinity for IL-18 with a rapid on-rate and a slow off-rate, and a dissociation constant (Kd) of approximately 0.4 nM (Kim et al. 2000).

IL-18BP belongs to the immunoglobulin superfamily.

The residues involved in the interaction of IL-18 with IL-18BP have been described through the use of computer modelling (Kim et al. 2000) and based on the interaction between the similar protein IL-1β with the IL-1R type I (Vigers et al. 1997).

IL-18BP is constitutively present in many cells (Puren et al. 1999) and circulates in healthy humans, representing a unique phenomenon in cytokine biology. Due to the high affinity of IL-18BP to IL-18 (Kd=0.4 nM) as well as the high concentration of IL-18BP found in the circulation (20 fold molar excess over IL-18), it has been speculated that most, if not all of the IL-18 molecules in the circulation are bound to IL-18BP. Thus, the circulating IL-18BP that competes with cell surface receptors for IL-18 may act as a natural anti-inflammatory and an immunosuppressive molecule.

IL-18BP has been suggested as a therapeutic protein in a number of diseases and disorders, such as psoriasis, Crohn's Disease, rheumatoid arthritis, psoriatic arthritis, liver injury, sepsis, atherosclerosis, ischemic heart diseases, allergies, etc., see e.g. WO9909063, WO0107480, WO0162285, WO0185201, WO02060479, WO02096456, WO03080104, WO02092008, WO02101049, WO03013577.

The prior art does not describe a process for the production of recombinant IL-18BP in CHO cells, nor IL-18BP compositions characterized by a specific glycosylation profile.

SUMMARY OF THE INVENTION

The present invention relates to the development of a process for producing recombinant Interleukin-18 binding protein (IL-18BP) in mammalian cells in a bioreactor under serum-free culture conditions comprising a cell propagation phase at about 37° C. and a production phase at a temperature ranging from about 29° C. to about 34° C.

In particular, an efficient perfusion production process has been developed for IL-18 binding protein (IL-18BP) that involves reduction of the perfusion rate during the production phase of a recombinant protein from mammalian cells in a bioreactor without significantly reducing the productivity of the recombinant protein product by the cells.

The perfusion process for producing recombinant Interleukin-18 binding protein (IL-18BP) in mammalian cells in a bioreactor under serum-free culture conditions comprising:

a) A cell propagation phase at 37° C. with a given perfusion rate (100%);

b) A production phase I at 33.5° C. at a perfusion rate that ranges from about 85 to about 65% or about 80 to about 70% or about 75% of the perfusion rate of the perfusion rate of step (a);

c) A production phase II at 32.5° C. at a perfusion rate that ranges from about 85 to about 65% or about 80 to about 70% or about 75% of the perfusion rate of the perfusion rate of step (a).

Additionally, an efficient fed-batch process has been developed for the production of IL-18BP, under serum-free culture conditions, comprising:

a. A cell propagation phase at 37° C.;

b. Optionally, an intermediate phase at 33° C.;

c. A production phase at 29° C.

The invention also relates to a composition comprising IL-18BP that is characterized by a specific glycosylation profile comprising about 15 to about 25% of unsialylated N-glycans, about 15 to about 25% of unsialylated N-glycans, about 15 to about 30% of mono-sialylated glycans, about 35 to about 55% of di-sialylated N-glycans, about 5 to about 15% of tri-sialylated N-glcyans and about 1 to about 5% of tetra-sialylated N-glycans.

The invention further relates to a composition comprising an IL-18BP that is characterized by a glycoform profile comprising about 0 to about 15% of basic glycoforms, about 15 to about 30% of less acidic glycoforms, about 40 to about 65% of acidic glycoforms, and about 10 to about 30% of highly acidic glycoforms.

BRIEF DESCRIPTION OF THE DRAWINGS

FIGS. 6A-6C: Sialylation by N-Glycan mapping (RP-HPLC profiles) in intermediate bulk samples at production day 47-48 of run-50 (FIG. 6A), run-75 (FIG. 6B) and run-100 (FIG. 6C).

DETAILED DESCRIPTION OF THE INVENTION

Figure 1:
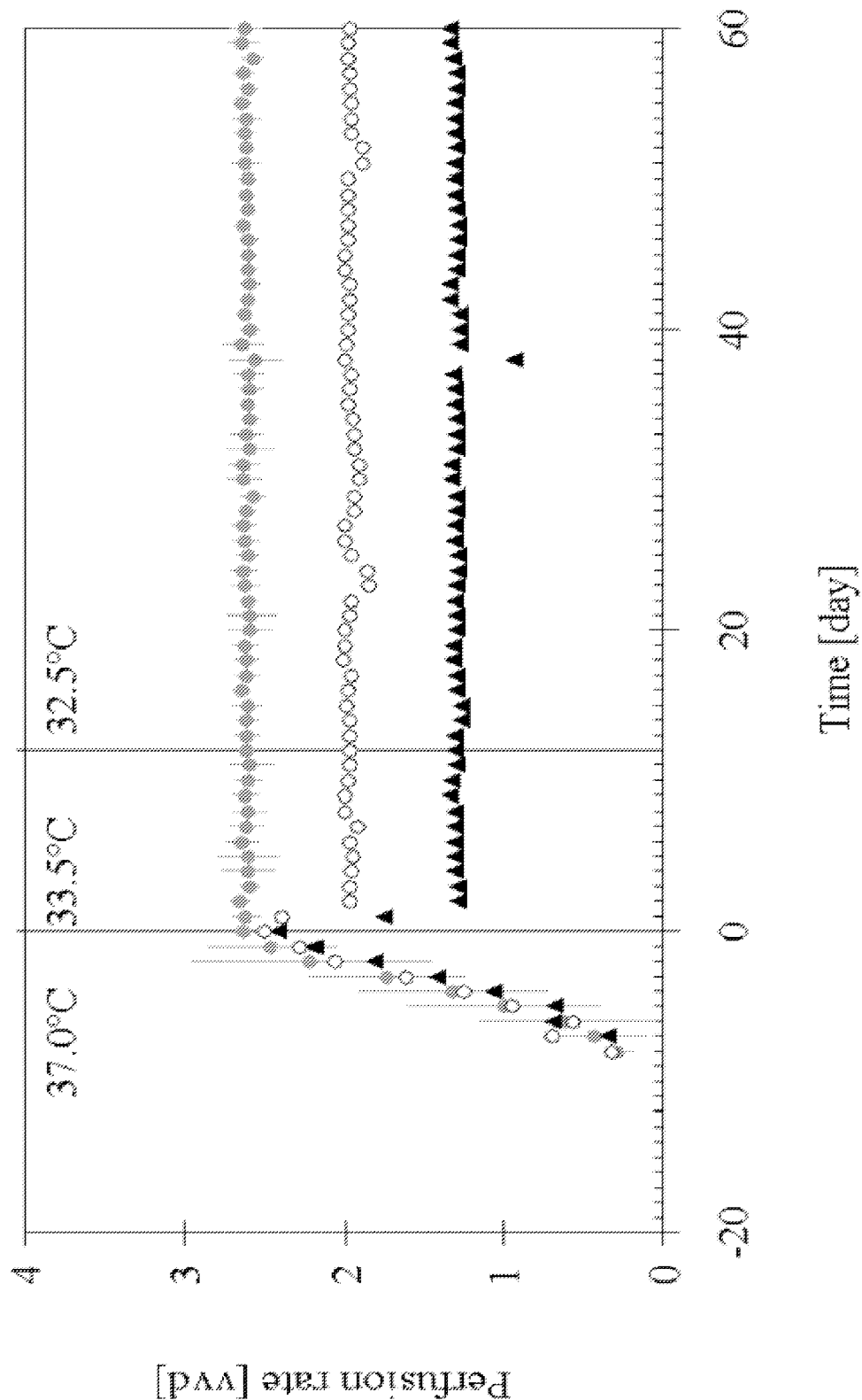
FIG. 1: Medium perfusion rate during continuous cultures of CHO cells in a packed-bed bioreactor according to example 1, with perfusion levels of 2.6 vvd (●), 2.0 vvd (○) and 1.3 vvd (▲). The bioreactor runs have been labelled as run-100 for 100% perfusion (●), run-75 for 75% perfusion (○) and run-50 for 50% perfusion (▲). The maximum perfusion rate of 100% corresponds to 2.6 vvd that were used as the reference conditions.

The present invention is based on the development of efficient processes for the production of recombinant IL-18BP in a bioreactor under serum-free cell culture conditions. Therefore, the present invention relates to a process for producing recombinant Interleukin-18 binding protein (IL-18BP) in mammalian cells in a bioreactor under serum-free culture conditions comprising a cell propagation phase at about 37° C. and a production phase at a temperature ranging from about 29° C. to about 34° C.

Any temperature between approximately 29 to approximately 34° C. will be suitable in the frame of the present invention such as e.g. 28, 28.5, 29, 29.5, 30, 30.5, 31, 31.5, 32, 32.5, 33, 33.5, 34, 34.5, 35° C.

Preferably, the invention relates to a perfusion process for producing recombinant Interleukin-18 binding protein (IL-18BP) in mammalian cells in a bioreactor under serum-free culture conditions comprising:

a) A cell propagation phase at 37° C. with a given perfusion rate (100%);

b) A production phase I at 33.5° C. at a perfusion rate that ranges from about 85 to about 65% or about 80 to about 70% or about 75% of the perfusion rate of the perfusion rate of step (a);

c) A production phase II at 32.5° C. at a perfusion rate that that ranges from about 85 to about 65% or about 80 to about 70% or about 75% of the perfusion rate of the perfusion rate of step (a).

It will be appreciated by the person skilled in the art that the perfusion rate of production phase (either I or 11 or both) may be e.g. at about 86, 85, 84, 83, 82, 81, 80, 79, 78, 77, 76, 75, 74, 73, 72, 71, 70, 69, 68, 67, 66 or 65, or 64% of the initial perfusion rate in step (a).

As shown in the examples below, it has been surprisingly found that in spite of the reduced perfusion rate, the cellular productivity of IL-18BP was substantially preserved.

It will also be appreciated by the person skilled in the art that the temperature may vary within certain limits, so as to be e.g. about 37.5° C. in step (a) or 34-33° C. in step (b) or 32-33° C. in step (c).

Typically, the Dissolved Oxygen concentration (DO) of a cell culture is maintained at about 50 to 70% of air saturation, and pH values vary between 6.5 and 7.5, preferably around 7.0.

The term "bioreactor", as used herein, refers to an apparatus or closed container that is used for generating biomolecules such as secreted proteins using the synthetic or chemical conversion capacity of a cell. Bioreactors include classical fermenters and cell culture perfusion systems. Bioreactors allow controlling various parameters during the cell culture process such as, e.g., the circulation loop flow, the temperature, the overpressure and/or the medium perfusion rate.

The term "serum-free medium", as used herein, refers to any medium that is free from components derived from animal serum such as e.g. fetal calf serum. Examples for commercially available serum-free media that can be used in accordance with the present invention include, e.g., SFM 90 (JRH, 67350), SFM 90.1 (JRH, 67350), Supmed300 or Supmed300 modified (JRH, 67350), DMEM (Gibco, 7490571), DMEM/F12 (Gibco, 99.5043), SFM CHO 3a (BioWhittaker), CHO PFM (Sigma, C6970), ProCHO 5, EX-CELL media such as EX-CELL 302 (JRH, Catalogue No. 14312-1000M) or EX-CELL 325 (JRH, Catalogue No. 14335-1000M), CHO-CD3 (Sigma, Catalogue No. C-1490), CHO III PFM (Gibco, Catalogue No. 96-0334SA), CHO-S-SFM II (Gibco, Catalogue No. 12052-098), CHO-DHFR (Sigma, Catalogue No. C-8862), ProCHO 5 (Cambrex, Catalogue No. BE12-766Q), SFM4CHO (HyClone, Catalogue No. SH30549.01), Ultra CHO (Cambrex, Catalogue No. 12-724Q), HyQ PF CHO (HyClone, Catalogue No. SH30220.01), HyQ SFX CHO (HyClone, Catalogue No. SH30187.01), HyQ CDM4CHO (HyClone, Catalogue No. SH30558.01), IS CHO-CD (Irvine Scientific, Catalogue No. #91119), IS CHO-V (Irvine Scientific, Catalogue No. #9197) and derivatives thereof. The composition of SFM 90, SFM 90.1, SupMed300, DMEM, DMEM/F12, SFM CHO 3$^a$ and CHP PFM is shown in Table I below.

The serum-free medium may preferably be a chemically defined medium, i.e., a medium prepared from purified ingredients and therefore whose exact composition is known. Specifically, chemically defined media do neither contain animal derived components nor undefined hydrolysates.

In accordance with the perfusion process of the invention, in a preferred embodiment the perfusion rate of step (a) has a dilution rate in the range of about 2 to 3 vvd, preferably about 2.5 vvd.

The term "dilution rate", as defined herein, refers to the dilution rate D expressed in vvd, calculated as liter of medium per liter of total system working volume per day (total volume=packed-bed+conditioning tank volume).

It will be appreciated by the person skilled in the art that the perfusion rate of step (a) may be e.g. about 1.9, 2.0, 2.1, 2.2, 2.3, 2.4, 2.5, 2.6, 2.7, 2.8, 2.9, 3.0 or 3.1 vvd.

Initial perfusion rates of about 2.6 or 2.5 or 2.75 vvd have shown to be particularly advantageous.

The length of the cell propagation phase of step (a), the production phase I of step (b) and the production phase II of step (c) will be readily determined by the person skilled in the art on the basis of parameters such as the initial cell seed, the type of cells used, the daily measured glucose consumption rate, the dilution rate, and process time. In accordance with the present invention, it is preferred that the cells are associated to carriers in the bioreactor, and that production phase I of step (b) is started at a glucose consumption rate of about 250 to 350 g of Glucose per kilogram of carrier.

The carrier that may be used in accordance with the processes of present invention may e.g. be a microcarrier. Microcarriers are small solid particles on which cells may be grown in suspension culture. Cells are capable of adhering and propagating on the surface of microcarriers. Typically, microcarriers consist of beads, the diameter of which is comprised between 90 μm and 300 μm. Microcarriers can be made of various materials that have proven successful for cell attachment and propagation such as, e.g., glass, polystyrene, polyethylene, dextran, gelatin and cellulose. In addition, the surface of microcarriers may be coated with a material promoting cell attachment and growth such as, e.g., e.g., N,N-diethylaminoethyl, glass, collagen or recombinant proteins. Both macroporous and non-porous microcarriers do exist. Macroporous surfaces give the cells easy access to the interior of the microcarrier after inoculation, and once inside of the microcarrier, the cells are protected from the shear forces generated by mechanical agitation and aeration in the bioreactor.

A further solid carrier that may be used in accordance with the present invention may e.g. be a Fibra-Cel® disk. Fibra-Cel® disks are disks of 6 mm in diameter that are composed of polyester non-woven fiber bonded to a sheet of polypropylene mesh (see, e.g., U.S. Pat. No. 5,266,476 and world wide web pages nbsc.com/products/miscellaneous/fibracel/ and nbsc.com/support/faqs/#fibra). Fibra-Cel® disks are usually treated electrostatically to facilitate suspension cells adhering to the disks and becoming trapped in the fiber system, where they remain throughout the cultivation process. Cell density and productivity achieved with cells grown on Fibra-Cel® disks can be up to ten times higher than with cells growing on microcarriers.

The cells expressing IL-18BP, that may be cultured in the bioreactor in accordance with the processes of the present invention may be any mammalian cell, including animal or human cells, such as e.g. 3T3 cells, COS cells, human osteosarcoma cells, MRC-5 cells, BHK cells, VERO cells, CHO cells, rCHO-tPA cells, rCHO-Hep B Surface Antigen cells, CHO-S cells, HEK 293 cells, rHEK 293 cells, rC127-Hep B Surface Antigen cells, Normal Human fibroblast cells, Stroma cells, Hepatocytes cells and PER.C6 cells.

It is preferred to use Chinese Hamster Ovary (CHO) cells for expression of IL-18BP in a process according to the invention.

The processes for production of IL-18BP of the invention preferably further comprises a step of collecting the cell culture supernatant (harvest).

In a further preferred embodiment, the processes further comprise one or more steps of purifying IL-18BP. Any suitable method may be used for the purification of IL-18BP, such as e.g. the purification processes described for IL-18BP in WO 2006/003134 or WO 2005/049649.

The purified IL-18PB product may then preferably be formulated into a pharmaceutical composition.

The invention also relates to an IL-18BP composition characterized by a sialylation profile comprising about 15 to about 25%, preferably about 19 to about 21% of unsialylated N-glycans, about 15 to about 30%, preferably about 20 to about 25% of mono-sialylated glycans, about 35 to about 55%, preferably about 39% to about 44% of di-sialylated N-glycans, about 5 to about 15%, preferably about 7 to about 10% of tri-sialylated N-glcyans and about 1 to about 5%, preferably about 2% to about 3% of tetra-sialylated N-glycans.

Such an IL-18BP composition is preferably obtained by the production processes of the invention.

The present invention further relates to a fed-batch process for producing recombinant Interleukin-18 binding protein (IL-18BP) in mammalian cells in a bioreactor under serum-free culture conditions comprising the steps of:
a. A cell propagation phase at 37° C.;
b. Optionally, an intermediate phase at 33° C.;
c. A production phase at 29° C.

The length of phases (a), optionally (b), and (c) can be readily determined by the person skilled in the art. Phase (a) will continue until an adequate number of cells has been generated, such as e.g. in the range of $10^5$ to $10^6$. Phase (b) will preferably be short, as it is a transient phase serving at adaptation of the cells to lower temperatures.

In a preferred embodiment, the total cell density in the production phase ranges between 4 to $8 \times 10^6$ cells per ml per day, preferably over at least 10 days of cell culture.

In a further preferred embodiment, the viability ranges between 100 and 80%, preferably over at least 10 days of cell culture.

It is further preferred that the protein productivity is higher than about 150 mg or about 250 mg or about 350 mg per 1 per day.

Preferred mammalian cells to be used in the frame of the process of the present invention are Chinese Hamster Ovary (CHO) cells.

The process preferably further comprises the steps of collecting the cell culture supernatant and/or purifying IL-18BP and/or formulating the IL-18BP into a pharmaceutical composition.

The invention also relates to an IL-18BP composition having a glycoform profile comprising about 0 to about 15% of basic glycoforms, about 15 to about 30% of less acidic glycoforms, about 45 to about 65% of acidic glycoforms, and about 10 to about 25% of highly acidic glycoforms.

The glycoform profile is characterized by way of capillary zone electrophoresis (CZE), indicating the extent of basic, less acidic, acidic and highly acidic glycoforms of IL-18BP. The method, and a definition of basic, less acidic, acidic and highly acidic glycoforms, can be taken from the examples below.

The hypothetical charge number Z is a parameter calculated according to a known formula (Hermentin et al., 1996, Gervais et al., 2003, see also the examples below), and characterizes the extent of sialylation of glycoproteins.

The IL-18BP composition of the present invention is characterized by a Z-number ranging between about 130 to about 160, preferably between about 140 and 155, more preferably between about 145 and about 150. Preferred Z-numbers for IL18BP are e.g. 139, 140, 141, 142, 143, 144, 145, 146, 147, 148, 149, 150, 151, 152, 153, 154, 155, or 156.

Although the IL-18BP compositions of the present invention may be produced by any process, such as e.g. perfusion processes operated with different parameter settings than described herein, e.g. at higher perfusion rates, the IL-18BP compositions of the present invention are preferably produced in the perfusion process or the fed-batch process of the present invention.

In accordance with the present invention, IL-18BP to be produced may be any IL-18BP from any species. Preferably, it is human IL-18BP.

Since IL-18BP is a soluble, secreted protein, it is released into the cell culture supernatant, either by means of its natural signal peptide, or by means of a heterologous signal peptide, i.e. a signal peptide derived from another secreted protein which may be more efficient in the particular expression system used, such as e.g. the GH signal peptide.

The term "IL-18 binding protein" is used herein synonymously with "IL-18BP". This term relates IL-18 binding proteins such as the ones defined in WO 99/09063 or in Novick et al., 1999. The term IL-18BP includes splice variants and/or isoforms of IL-18 binding proteins, as the ones defined in Kim et al., 2000, in particular human isoforms a and c of IL-18BP.

The term "IL-18PB", as used herein, further includes muteins, functional derivatives, active fractions, fused proteins, circularly permutated proteins and salts of IL-18BP as defined in WO 99/09063.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-18BP or encodes a viral IL-18BP (WO9909063) under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nim.nih.gov) and FASTA (Pearson W R, 1990).

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mutein has at least 40% identity or homology with the sequence of either an IL-18BP or a virally encoded IL-18BP homologue, as defined in WO 99/09063. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 4. More preferably, the synonymous amino acid groups are those defined in Table 5; and most preferably the synonymous amino acid groups are those defined in Table 6.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |

TABLE III-continued

Most Preferred Groups of Synonymous Amino Acids

| Amino Acid | Synonymous Group |
|---|---|
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

"Functional derivatives" as used herein cover derivatives of IL-18BPs or a viral IL-18BP, and their muteins and fused proteins, which may be prepared from the functional groups which occur as side chains on the residues or the N— or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

The term "salts" herein refers to both salts of carboxyl groups and to acid addition salts of amino groups of IL-18 inhibitor molecule, or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the IL-18 inhibitor, such as induction of IFN-gamma in blood cells.

The sequences of IL-18BP and its splice variants/isoforms can be taken from WO99/09063 or from Novick et al., 1999, as well as from Kim et al., 2000.

Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, described in WO 92/13095, for example.

A fusion protein of IL-18BP may e.g. comprise an immunoglobulin fusion, i.e. the inhibitor of IL-18 is a fused protein comprising all or part of an IL-18 binding protein, which is fused to all or a portion of an immunoglobulin. Methods for making immunoglobulin fusion proteins are well known in the art, such as the ones described in WO 01/03737, for example. The person skilled in the art will appreciate that the resulting fusion protein of the invention substantially retains the biological activity of IL-18BP, such as e.g. the binding to IL-18 which can be measured in in vitro assays described in the prior art such as e.g. WO 99/09063. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, IL-18BP is fused to the constant region of an Ig molecule, e.g. an Fc portion of an Immunoglobulin. Preferably, it is fused to heavy chain regions, like the CH2 and CH3 domains, optionally with the hinge region of human IgG1, for example. The Fc part may e.g. be mutated in order to prevent unwanted activities, such as complement binding, binding to Fc receptors, or the like.

The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

Further fusion proteins of IL-18BP may be prepared by fusing domains isolated from other proteins allowing the formation or dimers, trimers, etc. Examples for protein sequences allowing the multimerization of the polypeptides of the Invention are domains isolated from proteins such as hCG (WO 97/30161), collagen X (WO 04/33486), C4BP (WO 04/20639), Erb proteins (WO 98/02540), or coiled coil peptides (WO 01/00814).

The IL-18BP produced according to the process of the invention, or the composition according to the invention, may be intended for therapeutic use, i.e. for administration to patients. If IL-18BP is administered to patients, it is preferably administered systemically, and preferably subcutaneously or intramuscularly, or topically, i.e. locally. Rectal or intrathecal administration may also be suitable, depending on the specific use of IL-18BP.

For this purpose, produced IL-18BP may be formulated as a pharmaceutical composition, i.e. together with a pharmaceutically acceptable carrier, excipients or the like.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The therapeutically effective amounts of the active protein(s) will be a function of many variables, including the type of antagonist, the affinity of the antagonist for IL-18, any residual cytotoxic activity exhibited by the antagonists, the route of administration, the clinical condition of the patient (including the desirability of maintaining a non-toxic level of endogenous IL-18 activity).

A "therapeutically effective amount" is such that when administered, the IL-18 inhibitor results in inhibition of the biological activity of IL-18. The dosage administered, as single or multiple doses, to an individual will vary depending upon a variety of factors, including IL-18 inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

IL-18BP may be used in amounts in the ranges of about 0.001 to 100 mg/kg or about 0.01 to 10 mg/kg or body weight, or about 0.1 to 5 mg/kg of body weight or about 1 to 3 mg/kg of body weight or about 2 mg/kg of body weight.

IL-18BP may be administered daily or every other day or three times per week or once per week, at similar doses, or at doses increasing or decreasing with the time.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

IL-18BP may be administered prophylactically or therapeutically to an individual prior to, simultaneously or sequentially with other therapeutic regimens or agents (e.g. multiple drug regimens), in therapeutically effective amounts.

IL-18BP produced in accordance with the present invention may be used for preparation of a medicament for treatment and/or prevention of a number of diseases or disorders. Such diseases or disorders may e.g. be IL-18 mediated disorders. For instance, IL-18BP may be used for treatment and/or prevention of psoriasis, psoriatic arthritis, Crohn's Disease, inflammatory bowel disease, rheumatoid arthritis, liver injury such as alcoholic liver cirrhosis, sepsis, atherosclerosis, ischemic heart diseases, allergies, in particular delayed-type hypersensitivity, and closed head injury.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Perfusion Process for the Production of Recombinant, Human IL-18BP from Serum-free CHO Cell Harvest in Packed-bed Bioreactor This example describes a process based on the high cell density culture of recombinant CHO cells in a packed-bed bioreactor, in which the perfusion rate was adjusted according to cell growth requirements during the growth phase and then pronouncedly reduced during the production phase without compromising process productivity or protein quality.

The protein product produced by this process, IL-18BP, was characterized and turned out to have an advantageous N-glycan-profile.

A first-generation process had originally been designed with the aim to rapidly produce material for pre-clinical and early clinical trials.

This process was designed with a high perfusion rate of 2.6 vvd in order to supply the high cell density ($\sim 2.5 \cdot 10^7$ cell·ml$^{-1}$ of packed-bed) with fresh medium during production phase. In this first-generation process, product degradation was not a concern since the high dilution rate imposed to the culture maintained a low residence time of the product, IL-18BP, in the bioreactor environment.

At a later stage of the development, a reduction of the medium perfusion rate by −25% and −50% was tested in order to improve the process. A small-scale system was used to run the tests, and the selected conditions were then implemented at pilot scale in order to further produce material for clinical trials with an improved second-generation process.

Materials and Methods

Cell Culture—Experimental System

A packed-bed bioreactor (Ducommun et al. 2002a; Ducommun et al. 2002b) with Fibra-Cel® carrier (Bibby Sterilin, U.K.) was used to cultivate CHO cells (Laboratoires Serono S.A., Corsier-sur-Vevey, Switzerland) that express and secrete IL-18BP in a serum free medium (Sigma C-9486). In the small-scale system that was used to investigate a reduction of the perfusion rate, the bioreactor and packed-bed had a working volume of 15 and 5 litres respectively.

The bioreactor was perfused with 2.6 vvd (as defined in Table 1) during growth and production phase. This basic perfusion rate is chosen as the reference 100%, stated as run-100.

TABLE 1

Perfusion rates tested during the production phase for run-100, run-75 and run-50. Average of n replicates (±2 standard deviations for run-100).

|  | Perfusion rate ($l \cdot kg_{Fibra-Cel}^{-1} \cdot day^{-1}$) | Dilution rate (vvd*) | Replicates (n) |
| --- | --- | --- | --- |
| run-100 | 100 ± 3.5 | 2.6 ± 0.1 | 8 |
| run-75 | 75 | 2.0 | 3 |
| run-50 | 50 | 1.3 | 2 |

*The dilution rate D expressed in vvd is calculated as liter of medium per liter of total system working volume per day (total volume = packed-bed + conditioning tank volume).

These conditions were applied for all sets of bioreactor experiments: medium was perfused at 100% during growth phase at 37° C. The temperature was regulated at 37.0° C. during growth phase, and then reduced in two steps down to 32.5° C. The pH was regulated at 7.00 and Dissolved Oxygen concentration (DO) was maintained at 70% of air saturation throughout the culture.

Due to the fact that counting of cells and cell number determination in a packed-bed bioreactor is a complex and inaccurate analysis, we used Glucose Consumption Rate (GCR) as an indirect method to estimate cell growth and density in the packed-bed bioreactor. In our system, we have determined by direct cell counts on a number of packed-beds cultures that a GCR of 300 grams of glucose per kilogram of Fibra-Cele disks per day corresponds to approximately $2.5 \cdot 10^7$ cells per ml of packed-bed bioreactor volume (data not shown).

This stage has been defined as the end of the cell propagation phase at 37° C., and when GCR reached a level of 300 grams of glucose per kilogram of Fibra-Cele disks per day, the cultures were switched from 37.0° C. to the production mode by lowering the temperature to 33.5° C. At this stage, in one set of bioreactors the perfusion was kept at 100% (run-100) and the two other sets were performed with a medium perfusion rate of 75% (run-75) and 50% (run-50) of the maximal level, as summarized in Table 1. The temperature was further decreased to 32.5° C. at a later stage of the production phase to prevent further cell growth and to promote production.

In the results section, the bars displayed on the figures represent an interval of 4 standard deviations (±2 standard deviation) measured for the 8 replicates ran under the conditions of run-100.

Assays

Samples were removed daily during the culture. Glucose and lactate concentrations were quantified with an EML 105 analyzer (Radiometer Medical A/S, Brønshøj, Denmark).

The produced recombinant IL18BP was quantified with an ELISA test.

The quality of the recombinant protein was assessed with an RP-HPLC method, in combination with SDS-PAGE methods (ExcelGel SDS Homogeneous 12.5% (Cat# 80-1261-01, Pharmacia). The gels were stained specifically by Western Blot in order to detect high molecular weight (i.e. dimers, aggregates) or low molecular weight variants of the IL-18BP. Non-specific staining by Silver Stain was also used to assess the relative intensity of the IL-18BP compared to impurities after scanning (Scanner ARCUS 2, Afga) of individual bands in order to determine their relative intensity.

Protein sialylation, and in particular the abundance of neutral, mono-, di-, tri- and tetra-sialylated N-glycans was analysed by separation of the N-glycans according to their charge, as described in Gervais et al. 2003. The N-glycans were specifically cleaved from the IL-18BP by hydrazinolysis (N-glycanase E-5006B or E-5006C, Glyko Inc.), labelled with the 2-Aminobenzamide fluorescent dye (Signal 2-AB labelling kit K404, Glyko Inc.), and separated by a chromatography column before passing through a fluorescent detector. The proportions of N-glycans species could then be determined after integration of the HPLC peaks corresponding to neutral, mono-, di-, tri-, and tetra-sialylated forms.

Results

Reduction of Perfusion Rate

The first attempt was to reduce the perfusion rate from 2.6 vvd to 2.0 vvd and 1.3 vvd during the production phase (FIG. 1) and to follow its effect on cell metabolism, volumetric productivity and product quality.

Figure 2A:
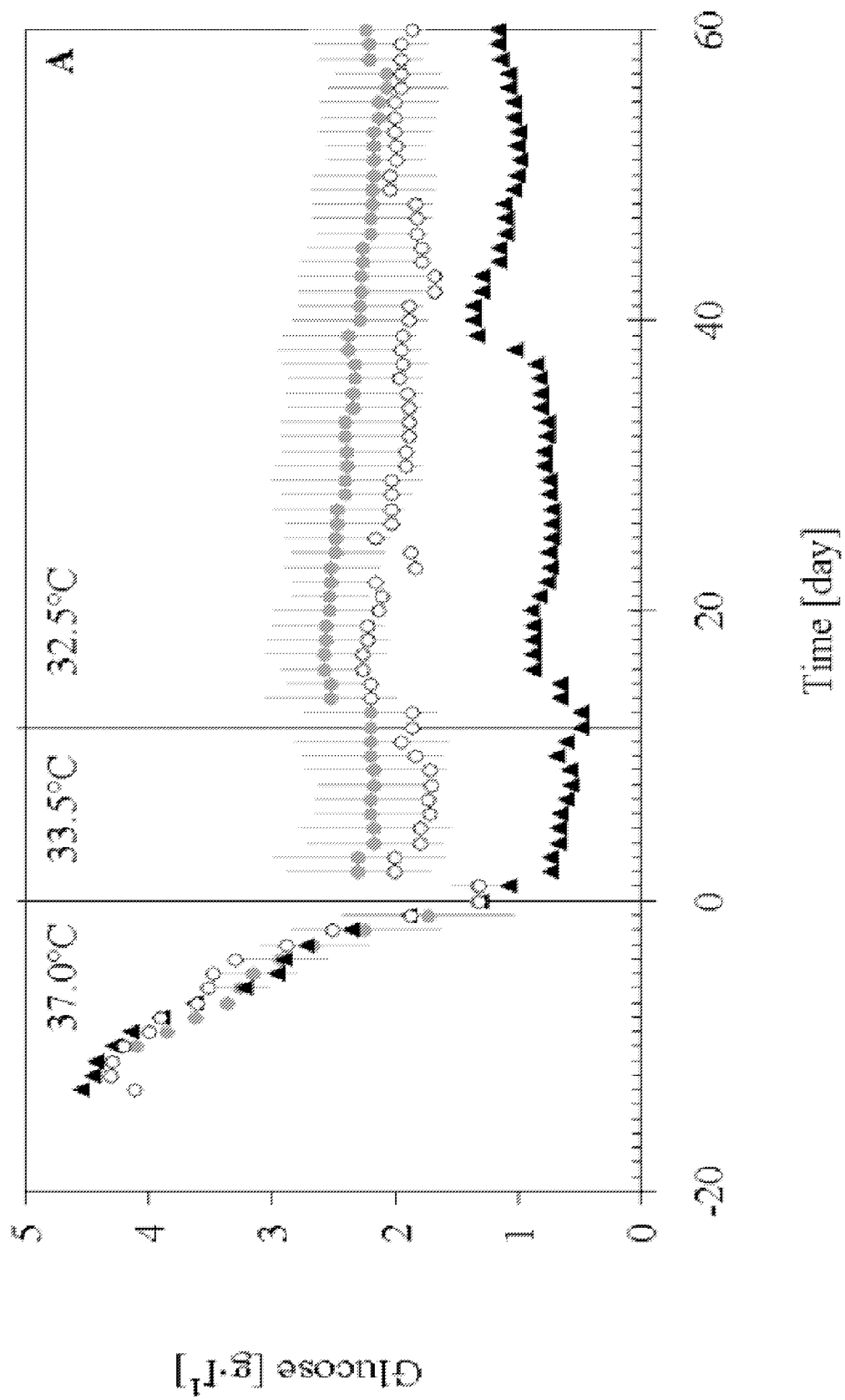
FIG. 2: Glucose (A) and lactate (B) concentration profiles during continuous cultures of CHO cells in a packed-bed bioreactor according to example 1, for medium perfusion rates of 100% (●) 75% (○) and 50% (▲).
Figure 2B:
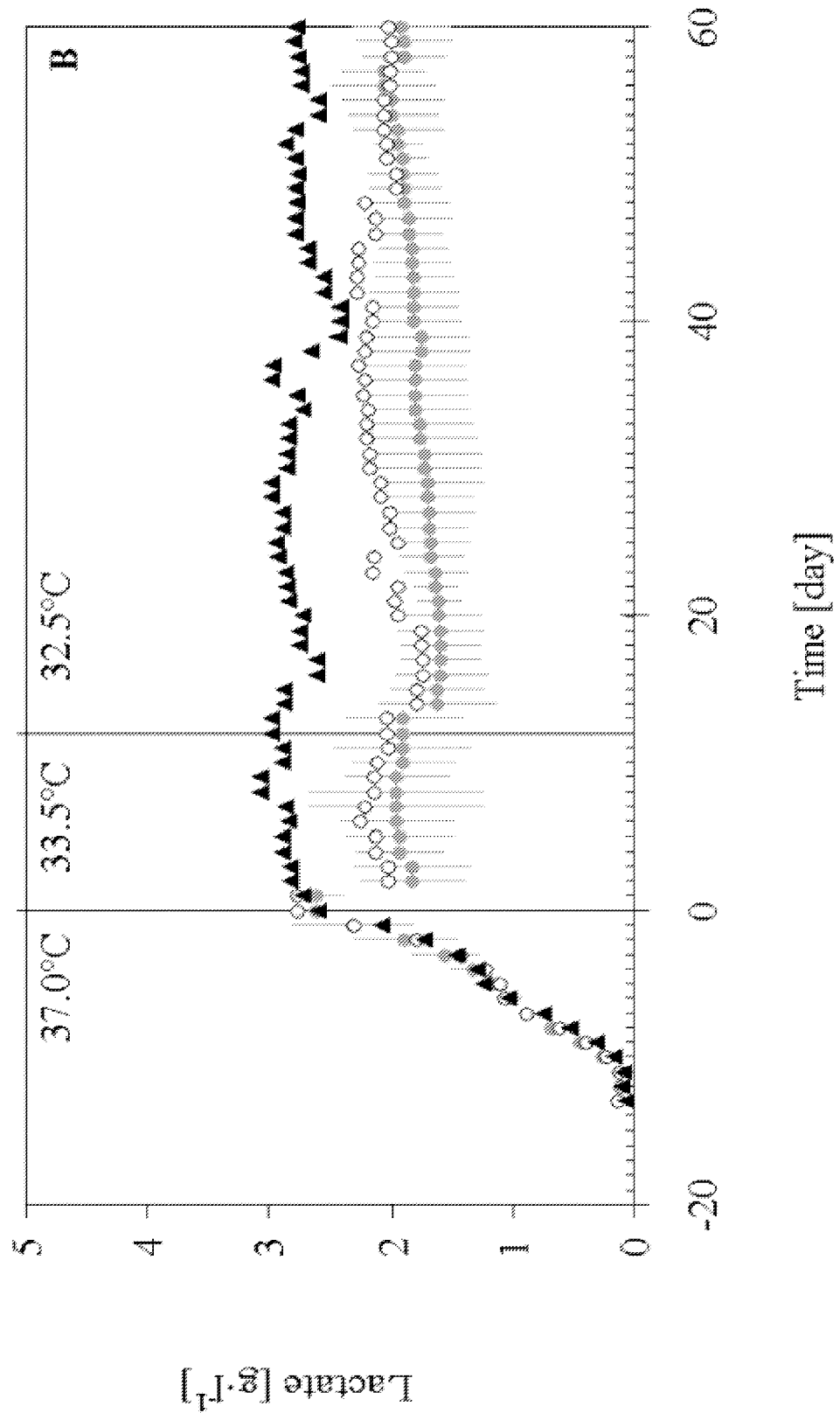

The concentration of glucose and lactate were measured for all three perfusion rates (FIGS. 2A and B), and the residual glucose level remained above 0.5 g/L.

Figure 3:
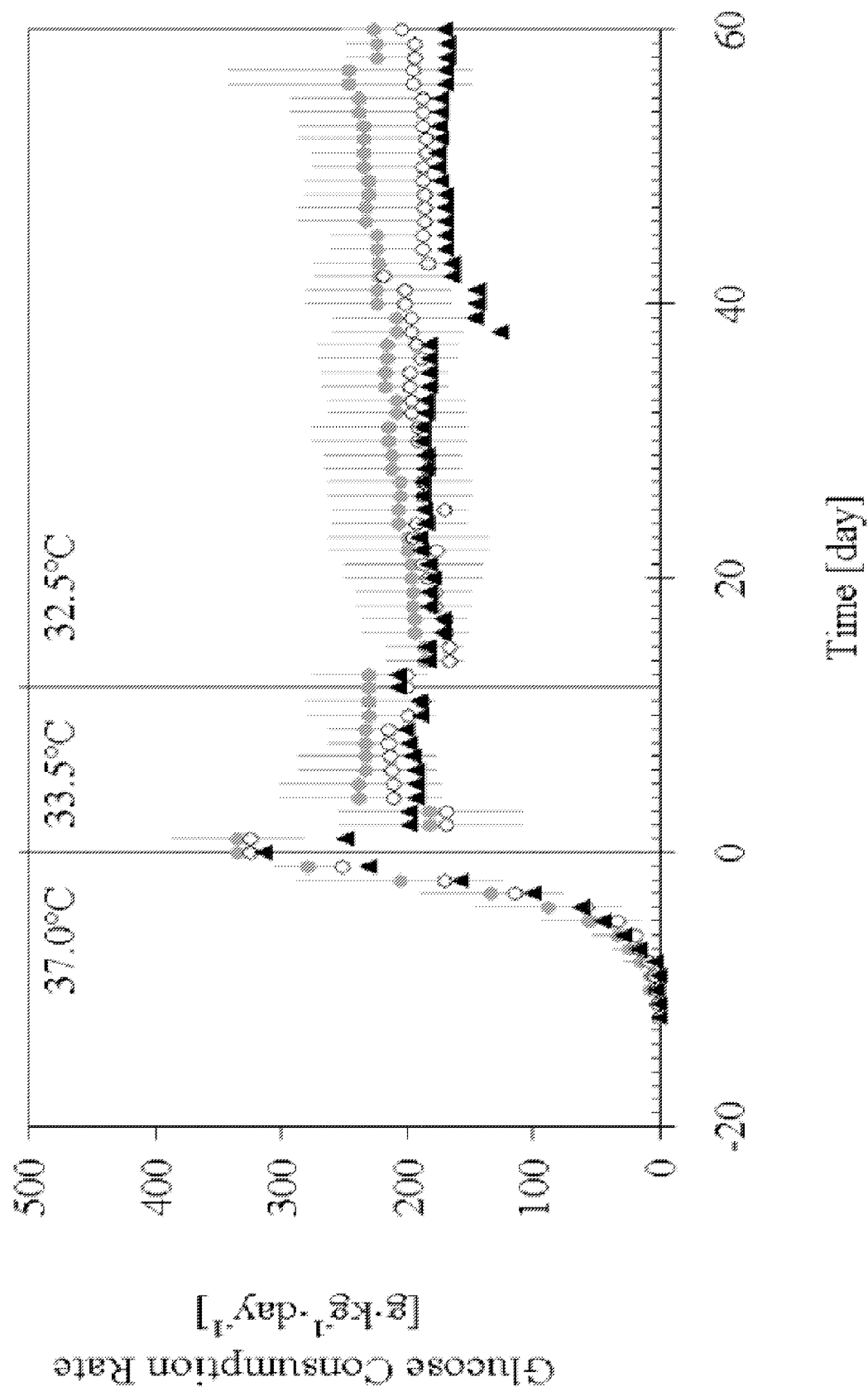
FIG. 3: Glucose Consumption Rate (GCR) profile during continuous cultures of CHO cells in a packed-bed bioreactor according to example 1, for medium perfusion rates of 100% (●) 75% (○) and 50% (▲). GCR is expressed in grams of glucose consumed per day and per kg of Fibra-Cel carrier.

The results in FIG. 3 show the glucose consumption rate (GCR) levels for the three sets of medium perfusion rate tested. These results indicate that a reduced perfusion rate induces a lower GCR of the culture. However, this effect was barely significant and when the medium perfusion rate was reduced by −25% and −50%, the average GCR measured over the 60-day production phase were reduced by −8% and −15% respectively (FIG. 3).

Figure 4:
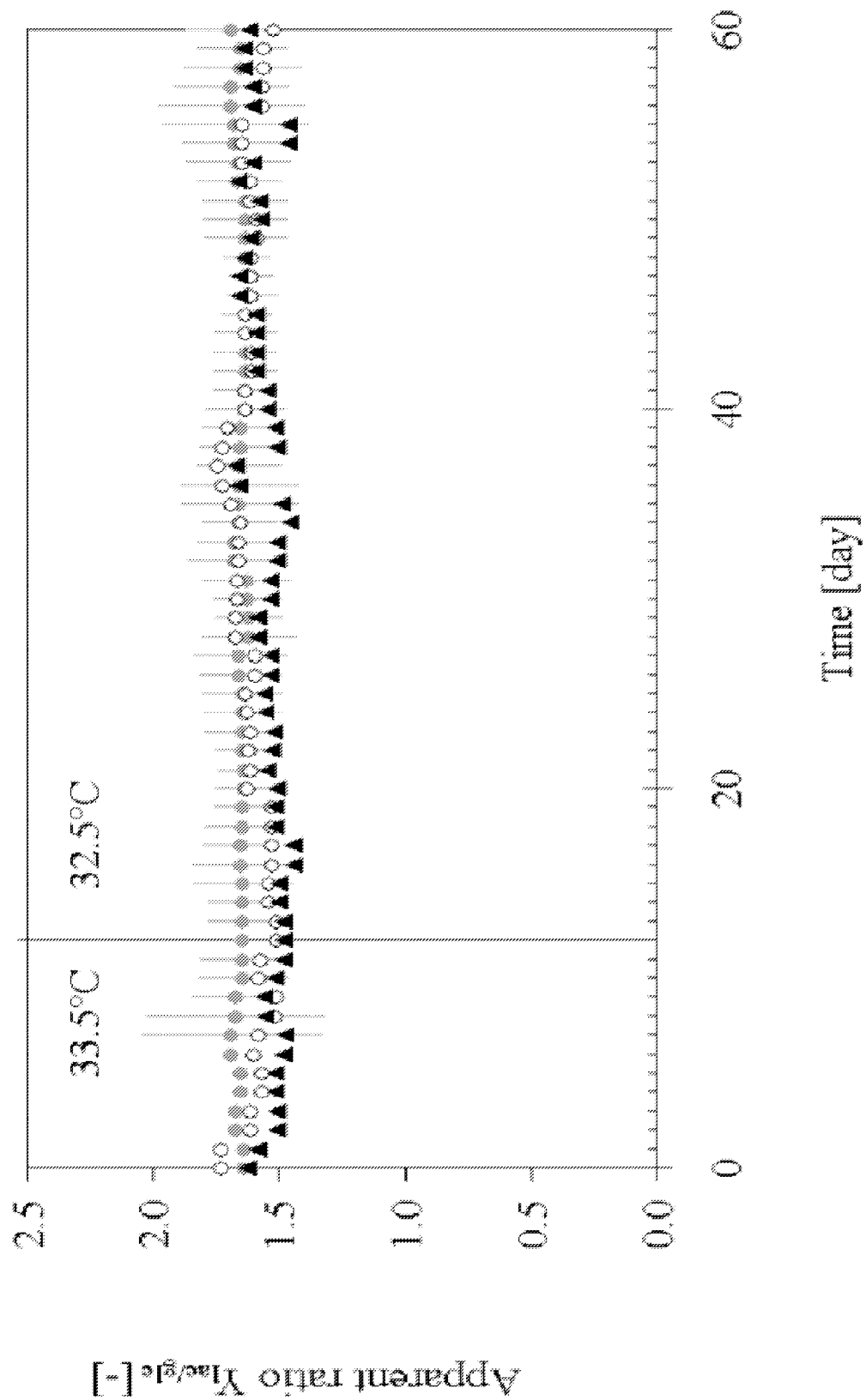
FIG. 4: Apparent lactate from glucose molar conversion ratio profile during continuous cultures of CHO cells in a packed-bed bioreactor according to example 1, for medium perfusion rates of 100% (●) 75% (○) and 50% (▲).

In parallel, the apparent molar ratio (FIG. 4) of glucose conversion to lactate $Y_{lac/glc}$ slightly decreased in response to lower perfusion rate but remained in a range of 1.55 to 1.65 mole of lactate produced per mole of glucose consumed. The differences observed for the $Y_{lac/glc}$ ratio were not statistically significant since all data points measured for the test runs at reduced perfusion rate are comprised within ±2 standard deviations of values obtained with the reference runs.

Process Productivity

Figure 5A:
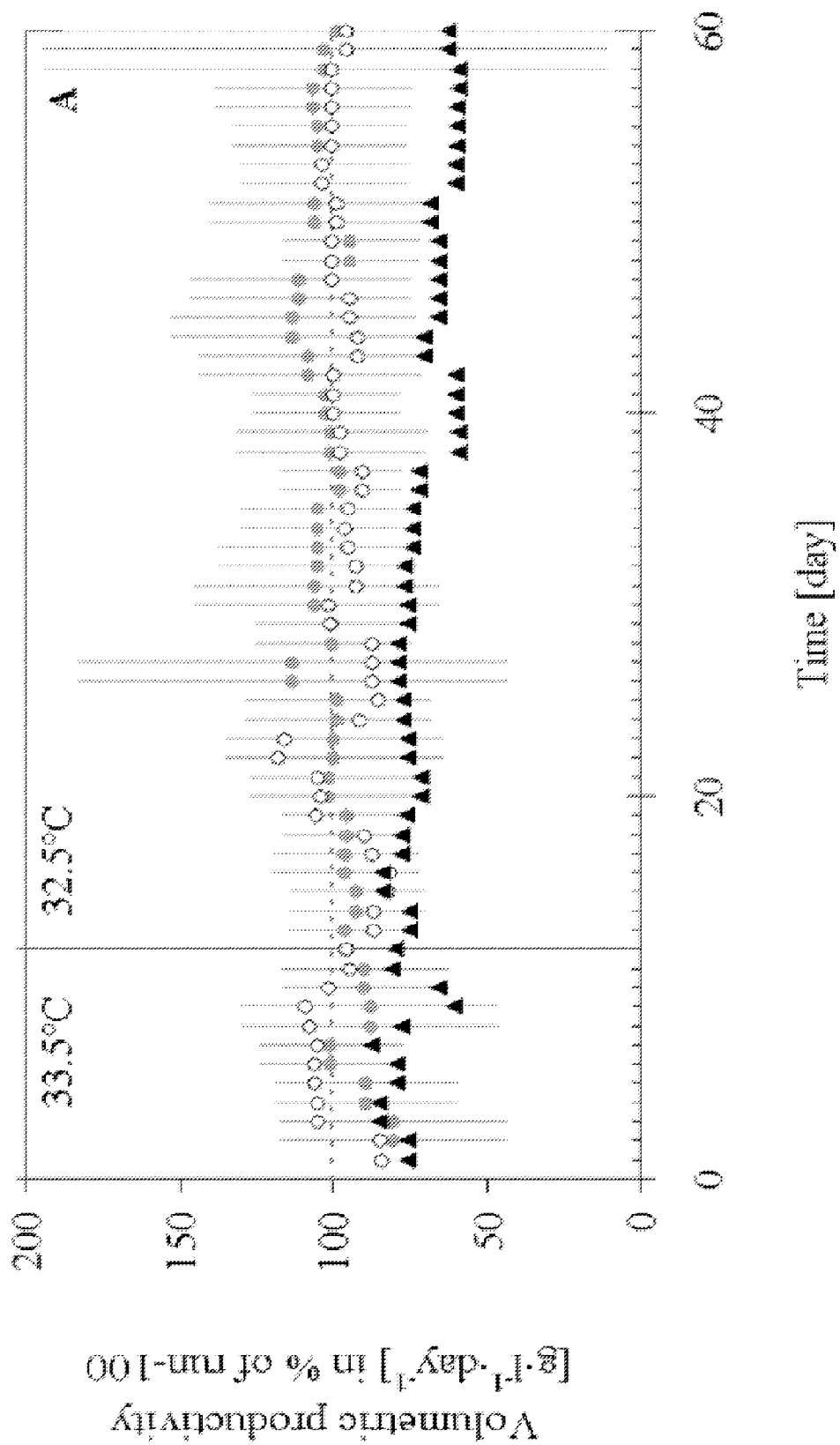
FIG. 5: Normalized productivity data (A) volumetric productivity in units of product per total culture volume per day, (B) cumulated product in units of product, (C) titre in units of product per total culture volume, for r-IL-18BP which is produced during continuous cultures of CHO cells in a packed-bed bioreactor according to example 1, for medium perfusion rates of 100% (●) 75% (○) and 50% (▲). To normalize the data, the average value obtained at 100% perfusion rate over the 60-day production phase was taken as 100% productivity (dotted line).

The results presented in FIGS. 5A, B and C show a comparison of the recombinant protein produced (volumetric productivity, total production, and titre) in the reference run-100 and in the runs with reduced medium perfusion.

When the medium perfusion rate was reduced by −25% and −50%, the average volumetric productivity was reduced by −3% and −30% respectively (FIG. 5A). The lower productivity result obtained for run-50 are statistically different from the reference conditions.

Another difference observed in FIG. 5A is the decline of the volumetric productivity over time along the production phase. A stable volumetric productivity was observed for run-100 and run-75, but in run-50 productivity declined over the duration of the 60-day production phase. More specifically, the productivity level of run-50 was 60% of the reference value at the end of the 60-day production phase.

Figure 5B:
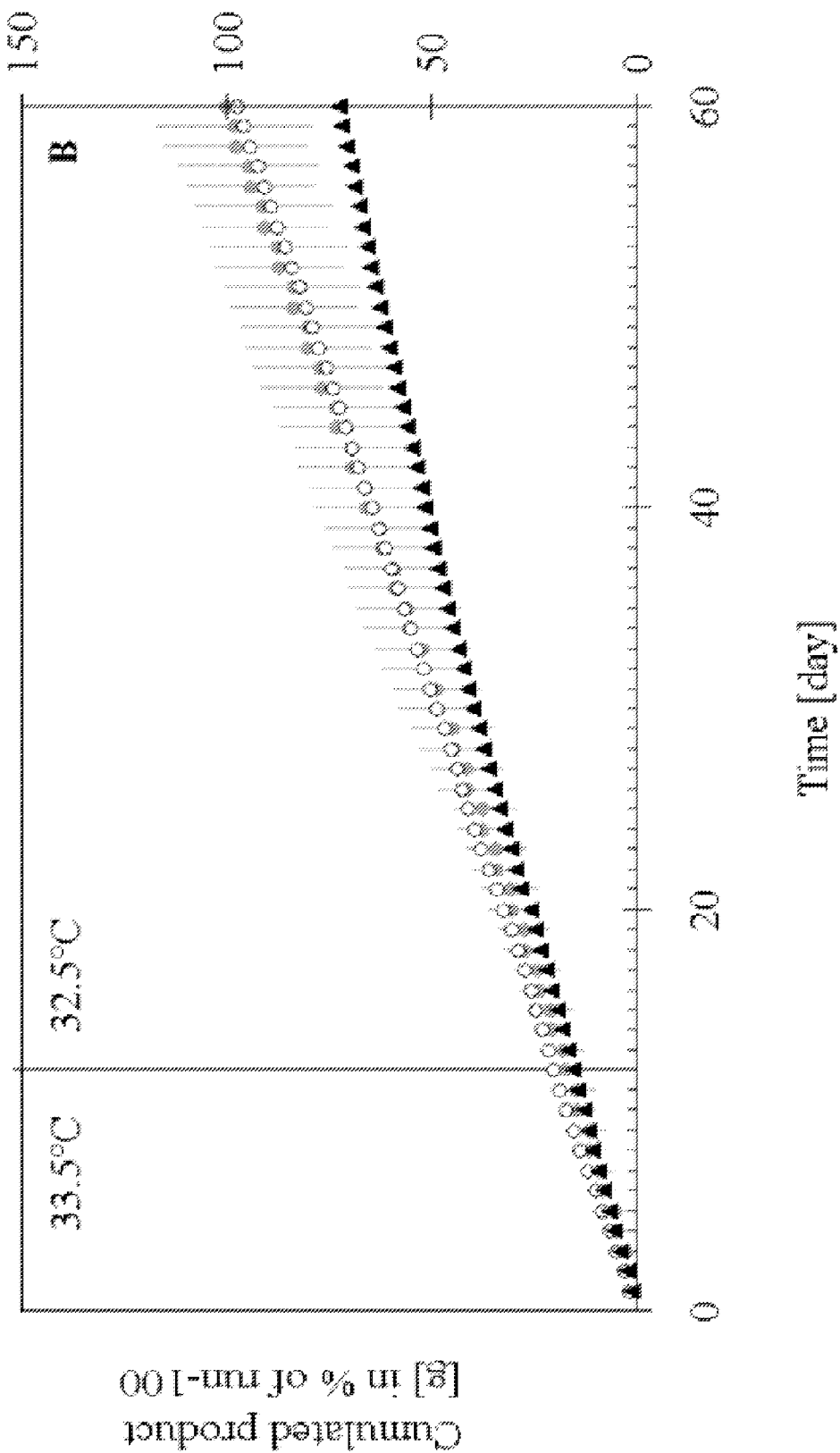

The lower productivity of run-50 is also shown on FIG. 5B, which represents the cumulated amount of product made over the 60-days production phase.

Figure 5C:
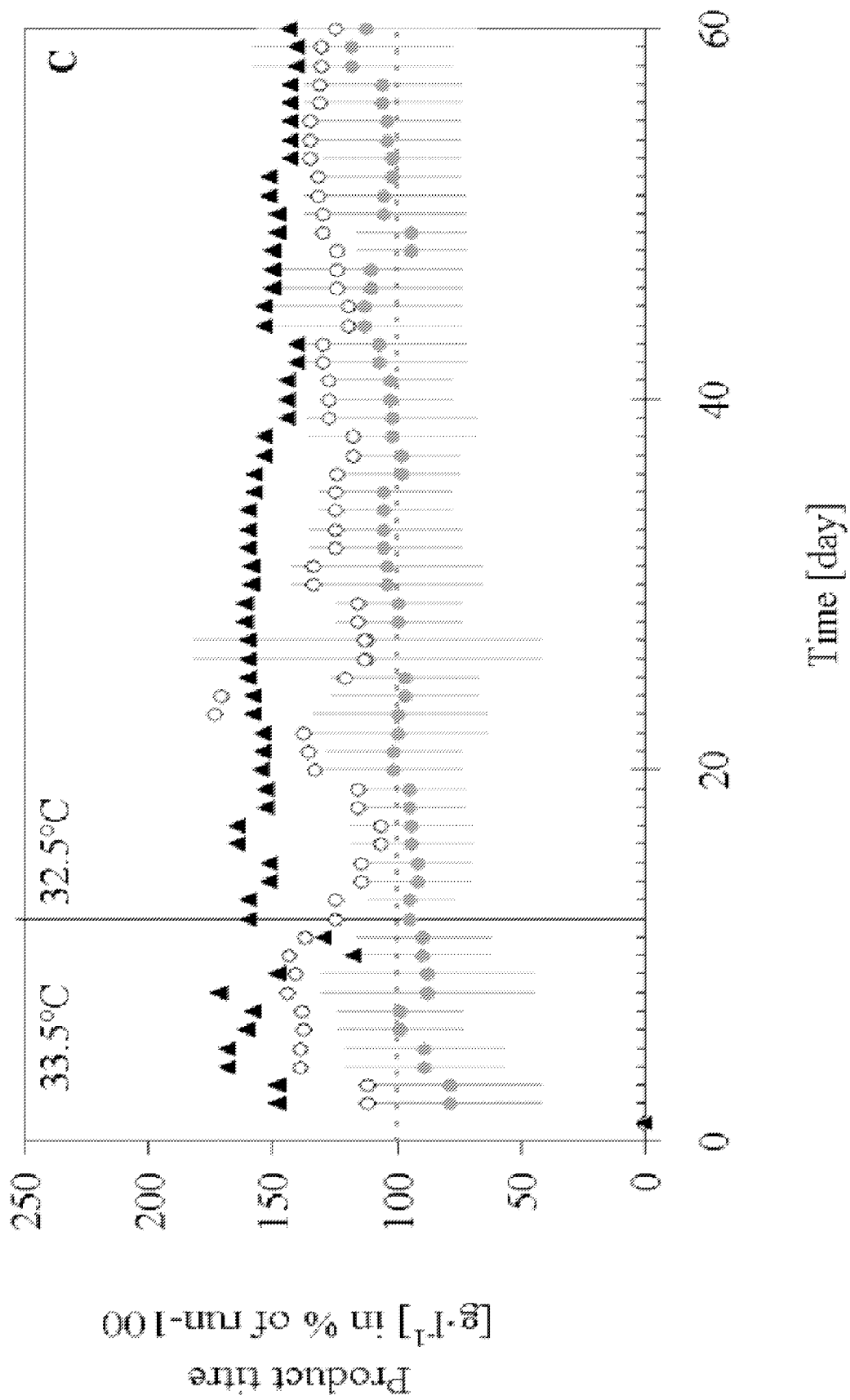

The corresponding titers measured for the different perfusion rates are presented in FIG. 5C, which shows that recombinant protein titers were increased by +25% and +50% respectively as opposed to the control when the perfusion was decreased by −25% and −50%.

Product Quality

With the reduction of the perfusion rate from 2.6 vvd, to 2.0 vvd and 1.3 vvd that was tested for run-100 run-75 and run-50, the residence time (t) of the recombinant protein was increased from 0.4 to 0.5 and 0.8 day respectively (t=1/D).

As a longer exposure to the environment in the bioreactor could potentially lead to a degradation of the recombinant protein, a stability study was done before initiating the tests in bioreactors. A sample of IL-18BP was spiked into cell culture medium, and the quality attributes of the IL-18BP were monitored after 1, 2 and 5 days of incubation at 37° C. Since no sign of product degradation was detected by the stability indicating method (data not shown), it was decided to proceed with the bioreactor experiments.

During the tests in bioreactors, the recombinant protein was purified to homogeneity at three points of the bioreactor runs (day 20, 40 and 60) in order to verify that the product quality was maintained for each perfusion rate investigated. The conditions of run-50 were considered as a worst case for protein degradation since this run had the lowest perfusion rate and the longest product residence time in the bioreactor.

To evaluate if product quality was affected by the reduced perfusion rate, final bulks of run-50 were analyzed by SDS-PAGE Silver Stain and SDS-PAGE Western Blot, and compared to the profile obtained in the reference conditions of run-100. The corresponding data obtained for one bulk produced with IL-18BP harvested at days 47-48 of the production phase of run-50 resulted in the expected single bands at a molecular weight of about 40 kDa (not shown). No modification of the IL-18BP quality attributes was detected for run-50 compared to run-100. The electrophoretic purity measured by SDS-PAGE Silver Stain was higher than 99% purity for all lanes, and no presence of aggregates or truncated forms could be detected as shown on the SDS-PAGE Western Blot (not shown).

The high level of purity (100%) of the IL-18BP produced was confirmed by RP-HPLC for run-100, run-75 and run-50.

Finally, the amount of impurities derived from the host CHO cell (Host Cell Proteins, HCP) in the produced protein was quantified by HCP-ELISA (data not shown) and was found consistent between run-50, run-75 and run-100.

N-glycan Profile

Samples of the produced recombinant IL-18BP were submitted to N-glycan mapping according to the method reported above, in order to quantify the proportion of the different sialylated forms of the protein of interest. The N-Glycan mapping results summarized in Table 2 show that comparable proportions of N-glycans are obtained for all perfusion rates tested. This is also illustrated by the corresponding HPLC profiles reported in FIG. 6.

TABLE 2

Fraction of differently sialylated N-Glycan molecules (given as % of the N-glycan groups) in semi-produced samples of drug substance for run-100, run-75 and run-50.

| | Fraction of differently sialylated N-Glycan molecules | | | | |
|---|---|---|---|---|---|
| | Neutrals (%) | Mono-sialylated (%) | Di-sialylated (%) | Tri-sialylated (%) | Tetra-sialylated (%) |
| run-100 | 19-21 | 21-29 | 39-44 | 7-11 | 2-4 |
| run-75 | 18-22 | 20-23 | 44-50 | 8-9 | 3-4 |
| run-50 | 19-21 | 20-25 | 45-48 | 8-10 | 2-4 |

A comparison of these data demonstrates that the product sialylation is not altered by the reduced perfusion rate, and the data obtained for run-75 and run-50 are clearly within the range obtained under the standard conditions of run-100.

Summary and Conclusions

In the present study, the optimal medium perfusion rate to be used for the continuous culture of a recombinant CHO cell line in a packed-bed bioreactor made of Fibra-Cel® disk carriers was determined.

A first-generation process had originally been designed with a high perfusion rate, originally operated with a perfusion of 2.6 vvd during production phase in order to supply the high cell density (~2.5·$10^7$ cell·$ml^{-1}$ of packed-bed) with sufficient fresh medium.

In order to improve the economics of this process, a reduction of the medium perfusion rate by −25% and −50% was investigated at small-scale. The best option was then implemented at pilot scale in order to further produce material for clinical trials with an improved second-generation process.

With a −25% reduction of the perfusion rate, the volumetric productivity was maintained compared to the first-generation process, but a −30% loss of productivity was obtained when further reducing the medium perfusion rate to −50% of its original level.

The protein quality under reduced perfusion rate conditions was analysed for purity, N-glycan sialylation level, abundance of dimers or aggregates, and showed that the quality of the final drug substance was comparable to that obtained in high perfusion conditions.

In this study it was established that the product quality was maintained upon reduction of the medium perfusion rate. The run with the lowest perfusion, run-50, has the longest residence time (t=0.8 day) and this is the worst case for protein stability since it leaves the product exposed to all potentially degrading activities present in the bioreactor environment for the longest time. Under these conditions we can consider that 99% of the protein will have a residence time in the bioreactor system shorter than 4 days (5t=4 day for run-50).

Since a stability study demonstrated that the IL-18BP could be stored for up to 4 days at 37° C. in crude harvest without significant alterations, it was anticipated that under the range of perfusion rates tested the product would not be degraded. This was confirmed by the results obtained in the bioreactor runs, as all lots of produced protein generated at production day-20, day-40 and day-60 of each perfusion conditions tested met the specifications established with reference material from run-100. Thus, in the study reported here, no sign of product degradation could be detected.

Glucose starvation is a typical cause of incorrect product sialylation (Goochee and Monica 1990). This effect has been studied for IFN-g produced from CHO cells, and the product glycosylation was found affected under low glucose residual levels below 0.1 g/L (Hayter et al. 1993), (Hooker et al. 1995).

In the conditions reported here, the IL-18BP sialylation was not affected due to the lower glucose concentrations reached during the production phase of run-75 and run-50. Without wishing to be limited to a specific explanation, this could be explained by the fact that the range of residual glucose concentrations (2.6 g/L to 0.5 g/L) reported here is still much higher than the value of less than 0.1 g/L glucose level (probably inducing some glucose starvation effect) for which incomplete sialylation of IFN-g was observed.

Based on the results obtained at small-scale, a reduction of −25% medium perfusion was implemented at pilot scale in the second-generation process, which enabled to maintain the same productivity and the same quality of the molecule, while reducing costs of media, material and manpower of the production process.

The −25% reduction on medium translated directly into a −25% saving on: the powder medium and side ingredients, the pre-filters and sterilizing filters, the sterile bags used for media storage after filtration, and the labour costs associated with medium preparation as fewer medium batches were needed.

As the IL-18BP titer in the crude harvest was increased by +25% in the second-generation process, the downstream processing benefited from similar savings: reduced manpower needs due to smaller volumes to handle, reduced production cycle time, optimisation of the equipment, etc (data not shown).

Conclusion

From the results obtained at small-scale it is clear that reduction of −25% in perfusion rate combined both benefits of maximizing productivity with a saving of −25% on medium consumption.

Further reduction of the perfusion rate to −50% led to reduced process productivity, which declined by −30% under such conditions. With the −50% perfusion rate conditions, volumetric productivity declined over the duration of the 60-day production phase whereas a stable productivity was maintained with the higher perfusion rates tested. Product stability remained comparable, irrespective of the perfusion rate used in the process.

Example 2

Fed-batch Process for the Production of Recombinant, Human IL-18BP from Serum-free CHO Cell Culture A fed-batch process with recombinant human IL-18BP expressing cells in suspension culture was developed as well. Three runs were performed in total, using bioreactors of 5 L (n=2) or 300 L (n=1) nominal volume.

In summary, the culture set points were: oxygen concentration of 50% air saturation, pH 7.0 and 6.90, temperature of 37.0° C. during growth phase and then reduced in two steps down to 29.0° C. During the course of the fed-batch culture, the serum-free basal medium (Sigma, S-9942) was gradually supplemented with a concentrated feed solution.

The parameters of the fed-batch process are summarized in Table 3.

TABLE 3

Fed-batch Manufacturing process scheme

| Time/WD* [day] | T [° C.] | pH [pHU] | Feed Feed-1 | Comments |
|---|---|---|---|---|
| −3 | | | | Transfer the wave-bag inoculum pool to the seed bioreactor[1] with a target VCs of: VCs** = 0.20 ± 0.05 mioCs/mL |
| 0 | | | | Transfer the seed bioreactor inoculum pool to the production bioreactor[2] with a target VCs of: VCs = 0.60 ± 0.10 mioCs/mL |
| 0 | 37 | 6.90 | +80 g/kg$_{Supernatant}$ | c(glucose) < 1.0 g/L[3] |
| ↓ | N/A | N/A | +30 g/kg$_{Supernatant}$ | c(glucose) < 5.5 g/L[4] |

TABLE 3-continued

Fed-batch Manufacturing process scheme

| Time/WD* [day] | T [° C.] | pH [pHU] | Feed Feed-1 | Comments |
|---|---|---|---|---|
| 4 | →33 | N/A | | |
| ↓ | N/A | N/A | | |
| 6 | →29 | N/A | | |
| ↓ | N/A | N/A | | |
| 20 | | | | Crude harvest clarification |

Figure 7:
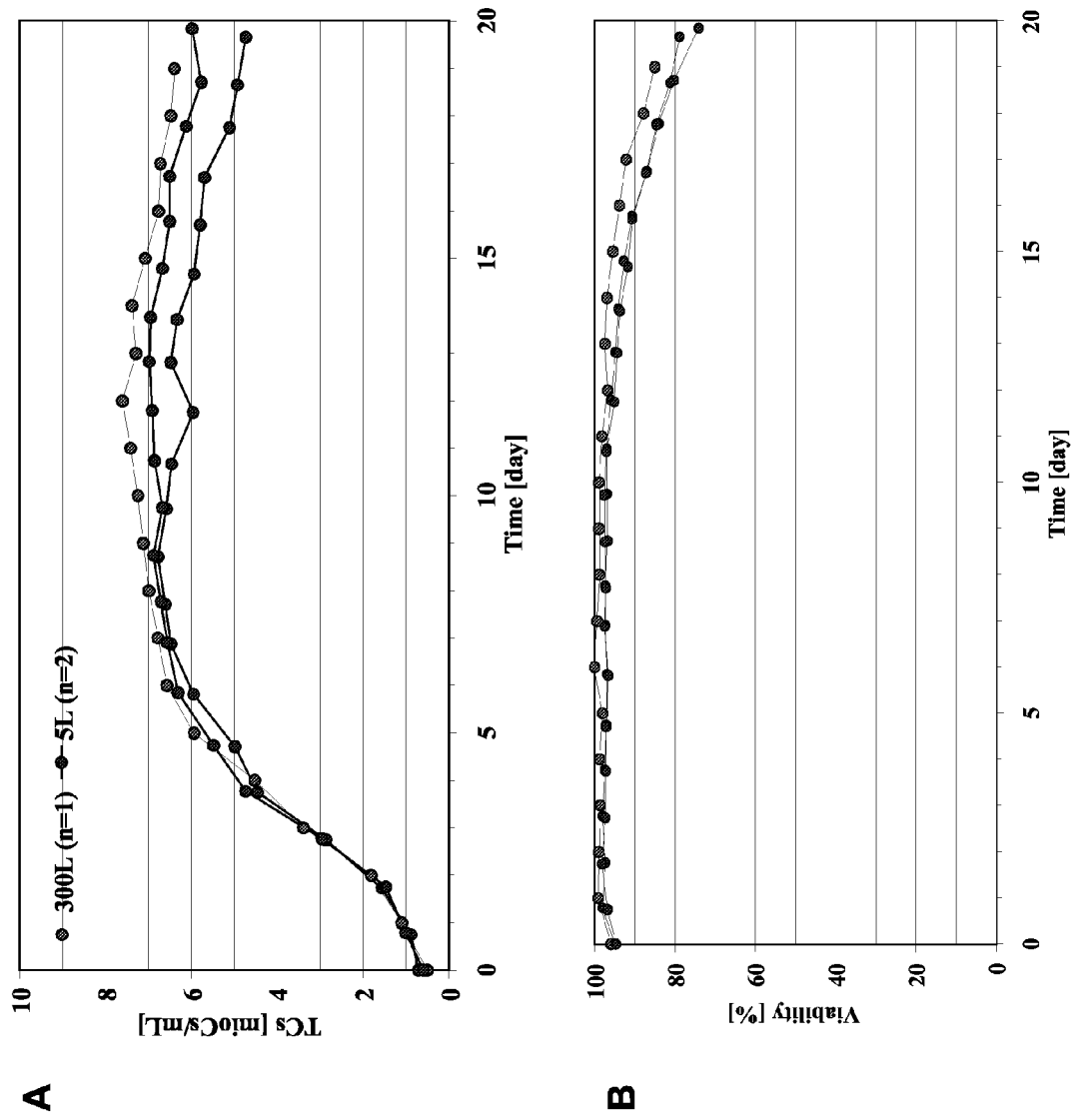
FIG. 7: Process performance of the fed-batch process according to example 2 in terms of (A) total cell-density, (B) viability, (C) residual glucose concentration, and (D) r-hIL-18BP titer.

[1] 5 L and 75 L bioreactor for small-scale (5 L) and pilot-scale (300 L) operation, respectively
[2] 5 L and 300 L bioreactor for small-scale (5 L) and pilot-scale (300 L) operation, respectively
[3] The first addition of Feed-1 occurs when c(glucose) < 1.0 g/L (+80 g/kg)
[4] The subsequent additions of Feed-1 occur each time when c(glucose) < 5.5 g/L (+30 g/kg)
*WD = working days
**VCs = viable cells Important performance indicators, namely total cell-density, viability, residual glucose concentration, and protein titer were analysed. As shown in FIG. 7(A) to (D), the final fed-batch process allowed growing up the clone to a maximum total cell-density of approximately 7.0 mioCs/mL and maintaining cell viability above 80% until working day 19, where the 300 L culture was harvested, clarified and captured. FIG. 7 (C) corresponds to the residual glucose concentration profiles, based on daily off-line measurements. These profiles illustrate the applied feeding strategy. For example, the first bolus addition of 80 g/kg of supernatant occurred in all three batches on working day 4 in order to raise residual glucose concentration up to more than 5.5 g/L. In a similar way, each subsequent addition of 30 g/kg of supernatant can easily be identified. Further, process productivity is shown in FIG. 7(D), with a consistent final r-hIL-18BP titre of 400 mg/L on working day 19. Protein quality was assessed on all three batches on working day 19.

Example 3

Sialylation Profile of rhIL-18BP Produced in Perfusion and the Fed-batch Process for CHO Cell Culture A further perfusion process for production of IL-18BP was set up. Perfusion runs were performed with a perfusion rate 2.75 vvd in a bioreactor containing a total volume of 160 L (including external column of 40 L) packed with 4.4 kg of Fibracel®-disks, at production temperatures of 33.5 or 32.5° C.

The IL-18BP produced in this perfusion process was compared to the material derived from the fed-batch process described in example 2.

Either perfusion or fed-batch supernatant were subjected to a capture step using affinity chromatography.

The post-capture IL-18BP material was analyzed for N-glycanation as described in Example 1 above.

The hypothetical charge number, the so-called Z-number, was calculated as described in Gervais et al. (2003). Briefly, the Z number is defined as the sum of the products of the respective areas (A) in the neutral, mono-, di-, tri-, tetra-, and pentasialylated region of the N-glycan species, each multiplied by the corresponding charge:

$$Z = A_{(neutral)} \times 0 + A_{(mono)} \times 1 + A_{(di)} \times 2 + A_{(tri)} \times 3 + A_{(tetra)} \times 4 + A_{(penta)} \times 5.$$

Figure 8:
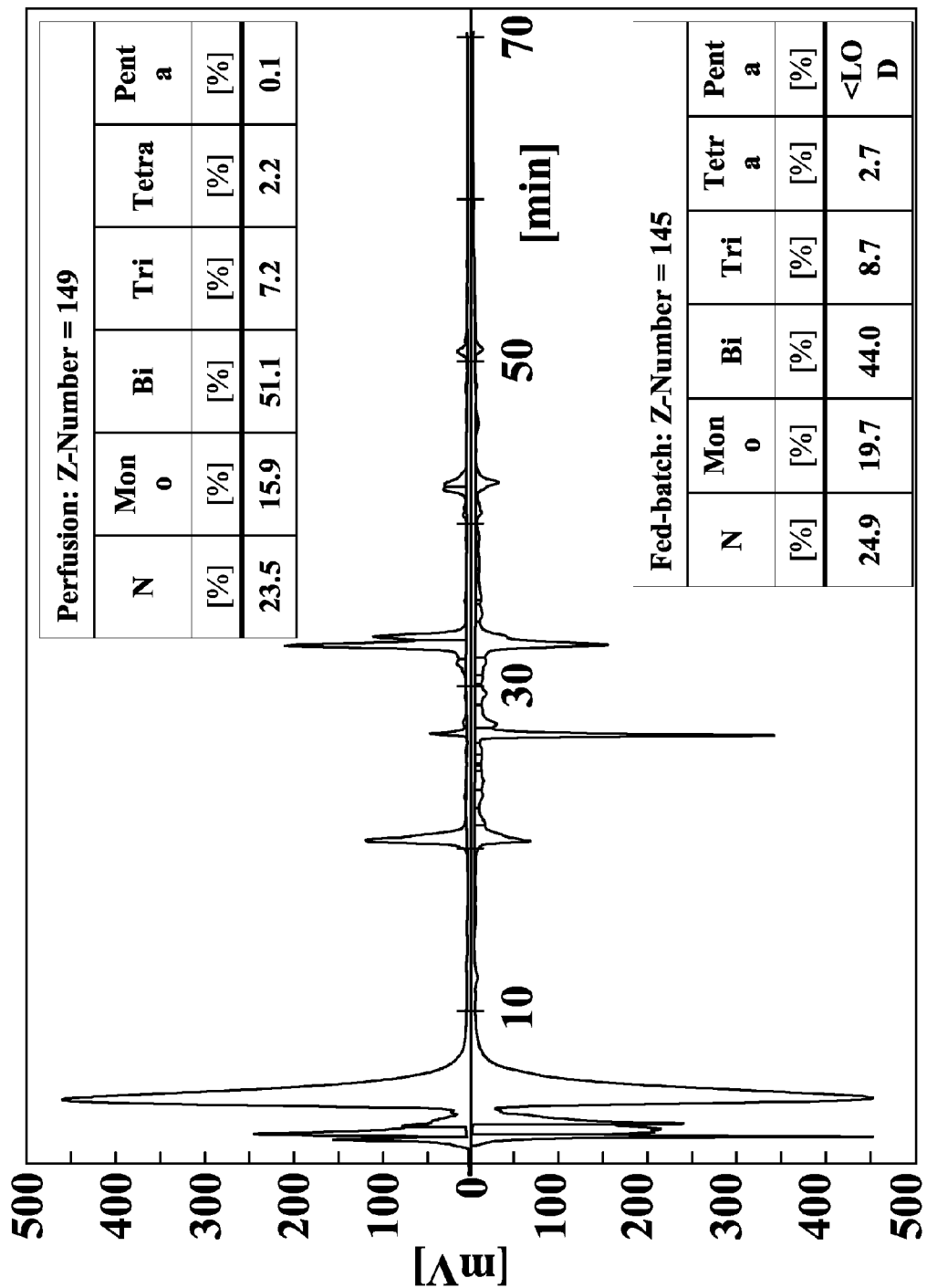
FIG. 8: Sialylation by N-Glycan mapping (RP-HPLC profiles) in purified IL-18BP prepared in a perfusion process (upper panel) or fed-batch (lower panel) process.

The results are depicted in FIG. 8, showing that despite some qualitative differences, mainly in the di-sialylated groups, the N-glycan mapping data indicate that the product sialylation was comparable for the perfusion (Z=149) and the fed-batch (Z=145) process conditions in terms of quantity.

The IL-18BP material ("crude harvest material"), either derived from the fed-batch or the perfusion process, was also analyzed by Capillary Zone Electrophoresis (CZE) for differentially glycosylated isoforms ("glycoforms"), according to the protocol described in detail below.

The isoform distribution was further compared to purified IL-18BP, either derived from fed-batch or the perfusion process.

Crude harvest material underwent a microcapture step on a Sep-Pak® tC2 cartridge (Waters) followed by a desalting step by Centricon® 10 (Millipore) ultrafiltration before being injected into the capillary. Purified IL-18BP was obtained essentially as described in patent application WO 2005/049649, albeit with a different capture step based on affinity chromatography. Briefly, the purification steps included metal ion affinity chromatography (on Chelating Sepharose FF), hydrophobic charge-induction chromatography (on Mep Hypercel), ion exchange chromatography (on CM-Sepharose FF, using the flow-through), hydrophobic interaction chromatography (on Phenyl Sepharose Fast Flow HS), and reverse phase chromatography (on Reverse Phase-Source 30 RPC). The finally purified material was directly applied to capillary without any further desalting step.

Method:
Solutions for CZE
5 mM phosphate CZE wash/run buffer:

Prepare by 1:10 dilution of 50 mM phosphate stock solution pH 7.0. Filter through 0.22 µm filter. Prepare fresh.

0.5 M NaOH (CZE washing solution):

Add 26.2 µL 50% NaOH to water, 1 mL total volume. Prepare fresh.

1M NaOH (CZE regeneration solution):

Add 52.4 µL 50% NaOH to water, 1 mL total volume. Prepare fresh.

Neutral Marker (dilution 1:10000)

Add 10 µL neutral marker stock solution to water, 1 mL total volume.

Add 10 µL of this neutral marker 1:100 dilution to water, 1 mL total volume.

Store for three months at 4° C.

CZE Analysis $\geq 20$ µL sample/reference are transferred into PCR vials containing 1/10 volume of neutral marker, and mixed by reverse pipetting, avoiding generating bubbles.

Electrophoretic Parameters:

The following reagents are added into separate vial holders, avoiding generating bubbles.

TABLE 4

Electrophoretic parameters for CZE

| Inlet reagents | Reagent volume | Outlet reagents | Reagent volume |
| --- | --- | --- | --- |
| Wash buffer | 1.2 mL | | |
| Run Buffer | 1.2 mL | Run Buffer (3.3.1) | 1.2 mL |
| Purified water | 1.2 mL | Purified water | 1.2 mL |
| CZE washing solution | 1.0 mL | | |
| CZE regenerating solution* | 1.0 mL | | |
| Sample | >22 µL/PCR Vial | | |
| | | Waste (purified water) 1 | 0.2 mL |
| | | Waste (purified water) 2 | 0.2 mL |
| Air* | | Empty Vial | |

*use only if required

TABLE 5

CZE Analysis time table

| Event | Value | Duration | Inlet Vial | Volume reagent | Outlet Vial |
| --- | --- | --- | --- | --- | --- |
| Rinse pressure | 20.0 psi | 2.00 min | Wash buffer | 1.2 mL | Waste 1 (0.2 mL) |
| Inject-pressure | 0.5 psi | 5.0 sec | Sample | $\geq$22 µL | Run Buffer (3.3.1) |
| Separate-Voltage | 25 KV | 30.00 min | Run Buffer | 1.2 mL | Run Buffer (3.3.1) |
| Rinse pressure | 20.0 psi | 1.00 min | Wash buffer | 1.2 mL | Waste 1 (0.2 mL) |
| Rinse pressure | 20.0 psi | 1.00 min | Purified water | 1.2 mL | Waste 1 (0.2 mL) |
| Rinse pressure | 20.0 psi | 1.00 min | CZE washing solution | 1.0 mL | Waste 2 (0.2 mL) |
| Rinse pressure | 40.0 psi | 2.00 min | Purified water | 1.2 mL | Waste 2 (0.2 mL) |
| Rinse pressure | 40.0 psi | 2.00 min | Wash buffer | 1.2 mL | Waste 2 (0.2 mL) |
| Wait | | | Wash buffer | 1.2 mL | Run Buffer (3.3.1) |

TABLE 6

CZE capillary regeneration timetable

| Event | Value | Duration | Inlet Vial | Volume reagent | Outlet Vial |
|---|---|---|---|---|---|
| Rinse pressure | 40.0 psi | 1.00 min | Purified water | 1.2 mL | Waste 2 (0.2 mL) |
| Rinse pressure | 40.0 psi | 10.00 min | CZE regenerating solution | 1.0 mL | Waste 2 (0.2 mL) |
| Rinse pressure | 40.0 psi | 4.00 min | Purified water | 1.2 mL | Waste 2 (0.2 mL) |
| Rinse pressure | 40.0 psi | 1.00 min | Wash buffer | 1.2 mL | Waste 2 (0.2 mL) |
| Rinse pressure | 0.5 psi | 30.00 min | Wash buffer | 1.2 mL | Waste 2 (0.2 mL) |
| Wait | | | Run Buffer | 1.2 mL | Run Buffer (3.3.1) |

Capillary length to detector/total length 50/60 cm
Polarity positive to negative (forward)
Temperature capillary = 25 ± 2° C.
sample tray =10 ± 2° C.
Detection 214 nm Injection Protocols There should be at least three injections of the Standard Reference material for the purpose of capillary conditioning.
  Standard Reference 1 (start)
  Single injection of sample 1
  Single injection of sample 2
  Single injection of sample 3
  Single injection of sample 4
  Standard Reference 2 (end)

NOTE: To increase reproducibility, a maximum of 4 samples can be analyzed in one sequence between reference 1 and reference 2 by using the same CZE running buffer.

Alternatively two bracketing references can be used for each sample as described below.

At least three injections of the Standard Reference material are done for the purpose of capillary conditioning.
  Standard Reference (start 1)
  Single injection of sample 1
  Standard Reference (end1/start2)
  Single injection of sample 2
  Standard Reference replicate (end2/start3)
  Single injection of sample 3
  Standard Reference replicate (end3)
  Data Analysis The Standard Reference material is used for comparison of sample data.

The overlaid and stacked electroferograms of sample/s and both bracketing Reference standard (start/end) are printed out and archived.

Determination of Migration Times MT2 and MT3

The migration times MT2 and MT3 at the left and right valleys of −3 and +3 peaks of the Reference Standard (Start) are determined. The 0 peak is the principal peak of the reference.

Isoform Classification Due the high acidity of IL-18BP glycoprotein profile, the isoforms between MT2 and MT3 are named "acidic isoforms". Isoforms with migration times higher than MT3 are named "highly acidic isoforms". Isoforms with migration times lower than MT2 are named "less acidic isoforms".

In some circumstances, it might be necessary to add the class of "basic isoforms" defined as isoforms with migration times lower then MT1.

Isoforms Abundance Estimation

The reference and each sample are analyzed by using the functions: manual peak between MT1-M2, MT2-MT3 and MT3-MT4; the manual baseline between 5 and 28 minutes and integration OFF between 0 and MT1 and between MT4 and 30 minutes. Manually modify the functions Width and Threshold to obtain an integration of three groups of peaks between MT1-M2 (less acidic isoforms), MT2-MT3 (acidic isoforms) and MT3-MT4 (highly acidic isoforms) similar to that showed above for the Reference Standard.

$$\% \text{ isoform abundance} = \frac{\text{area}(MT1\text{-}MT2 \text{ or } MT2\text{-}MT3 \text{ or } MT3\text{-}MT4)}{\text{Total area}(MT1\text{-}MT4)}$$

When necessary, the group of peaks corresponding to "basic isoforms" defined as isoforms with migration times lower than MT1, is added, and the above formula corrected accordingly.

Figure 9:
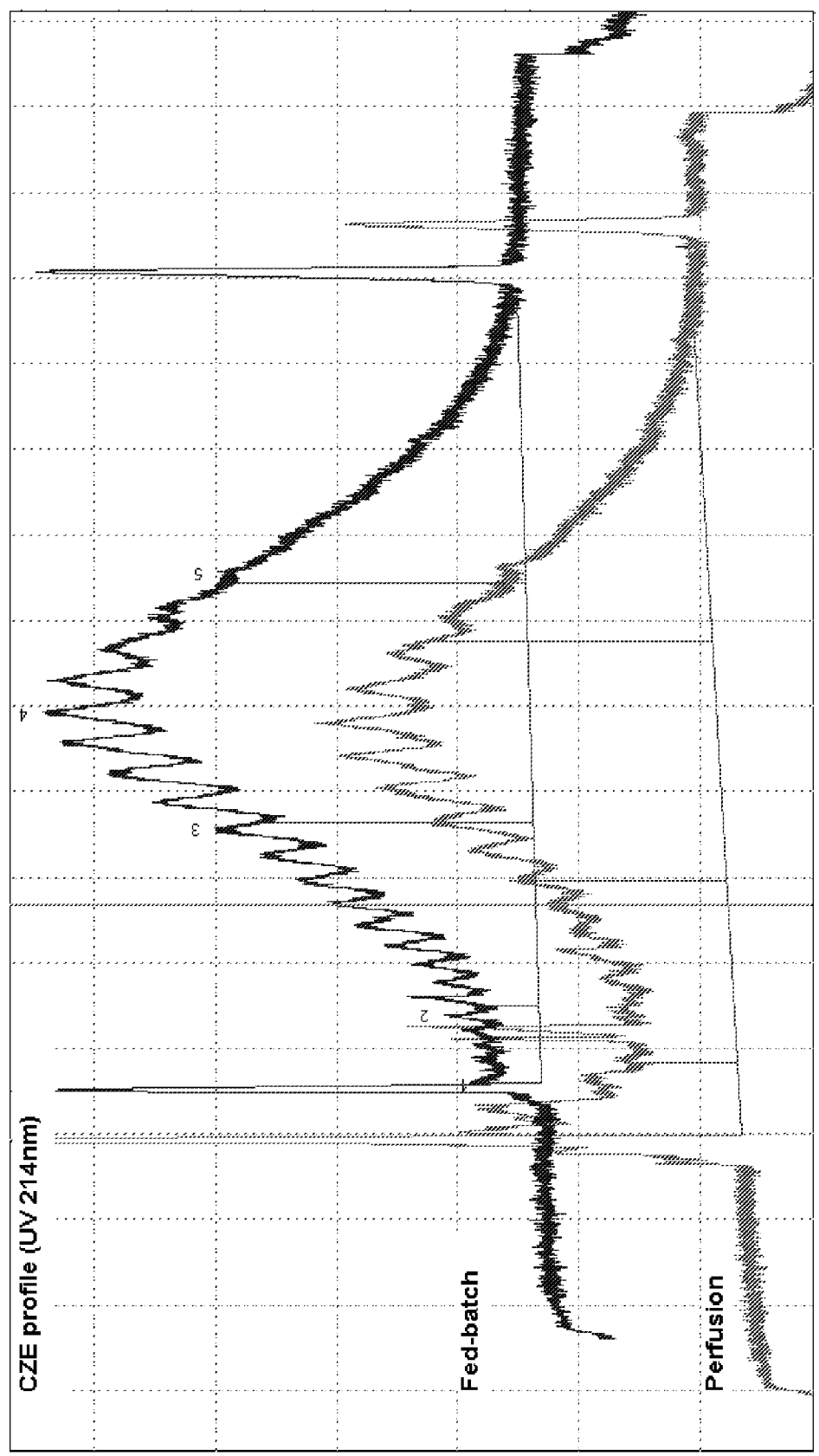
FIG. 9: Comparison of Capillary Zone Electrophoresis (CZE) profiles obtained from two separate analytical sequences, for: a (pre-treated) crude harvest sample from the fed-batch process (top), and a (pre-treated) harvest sample from the perfusion process (bottom).
Figure 10:
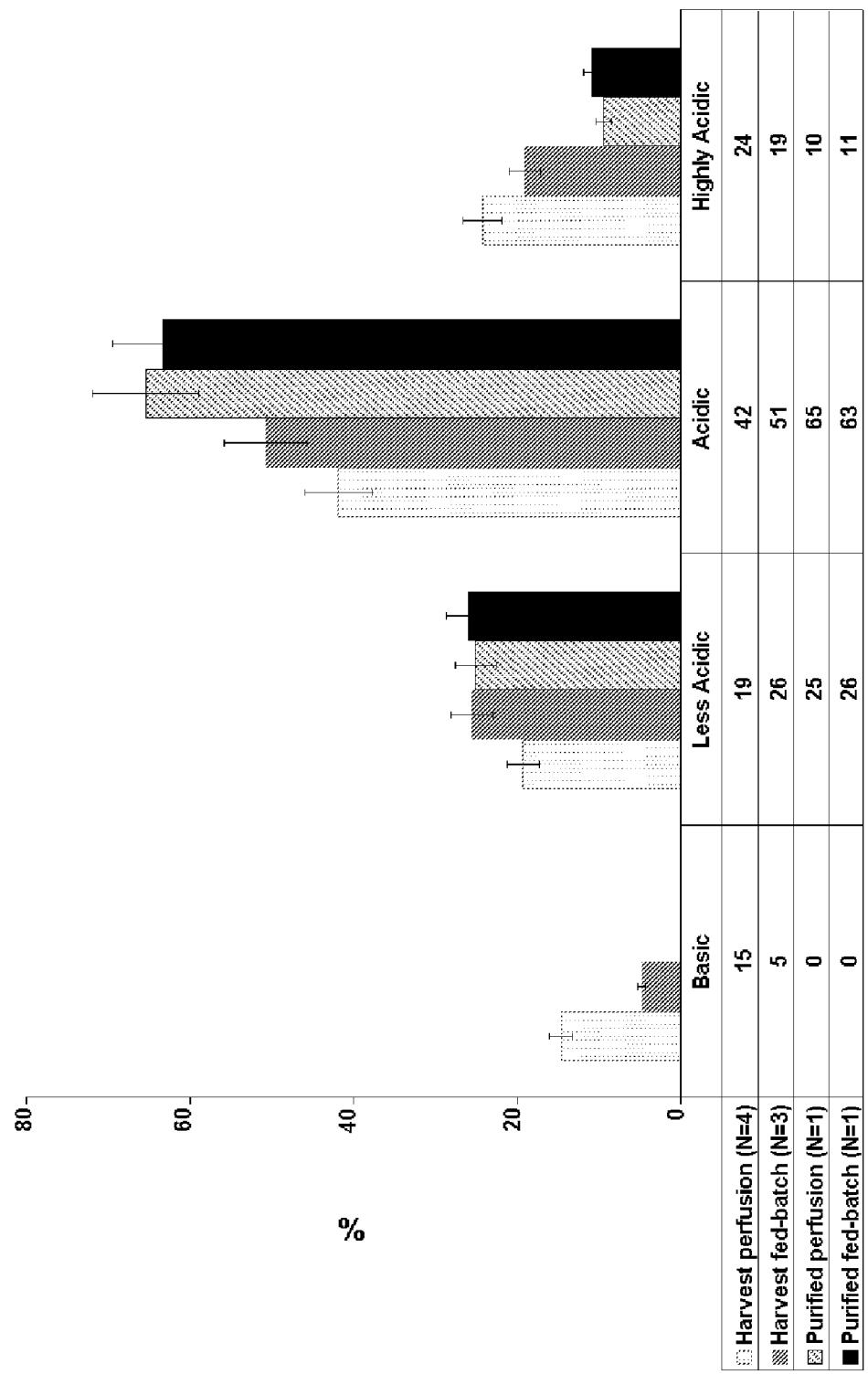
FIG. 10: Distribution of isoforms (given as % of all forms of the target molecule) by Capillary Zone Electrophoresis (CZE) in pre-treated crude harvest samples (dotted and grey) and purified (hatched and black) samples of IL-18BP for perfusion runs (dotted and hatched) and fed-batch runs (grey and black). The error bars correspond to the ±10% variability of the CZE method.

Results:

This CZE method was applied to crude harvest samples (FIG. 9) and to purified samples for both perfusion and fed-batch process. Despite some differences observed for the pre-treated harvest samples (e.g. higher proportion of basic isoforms with the perfusion process), these basic isoforms were successfully removed by ion exchange chromatography during the purification process (data not shown). Hence, for the purified product, a comparable isoforms profile was obtained for both processes (FIG. 10).

REFERENCES

Altschul S F et al (1990) Basic local alignment search tool. J Mol Biol, 215, 403-410.

Altschul S F et al (1997) Gapped BLAST and PSI-BLAST: a new generation of protein database search programs. Nucleic Acids Res., 25:389-3402

Andersen D C, Bridges T, Gawlitzek M, and Hoy C (2000) Multiple cell culture factors can affect the glycosylation of Asn-184 in CHO-produced tissue-type Plasminogen Activator. Biotechnol Bioeng 70 1: 25-31.

Chuppa S., Tsai Y.-S., Yoon S., Shackleford S., Rozales C., Bhat R., Tsay G., Matanguihan C., Konstantinov K., and Naveh D. (1997) Fermentor temperature as a tool for control of high-density perfusion cultures of mammalian cells. Biotechnol Bioeng 55 2: 328-338.

Devereux J et al (1984) A comprehensive set of sequence analysis programs for the VAX Nucleic Acids Res, 12, 387-395.

Dowd J. E., Kwok K. E., and Piret J. M. (2001) Glucose-based optimization of CHO-cell perfusion cultures. Biotechnology and Bioengineering 75 2: 252-256.

Ducommun P., Kadouri A., von Stockar U., and Marison I. W. (2002a) On-line determination of animal cell concentration in two industrial high-density culture processes by dielectric spectroscopy. Biotechnology and Bioengineering 77 3: 316-323.

Ducommun P., Ruffieux P.-A., von Stockar U., and Marison I. W. (2002b) Monitoring of temperature effects on animal cell metabolism in a packed bed process. Biotechnol Bioeng 77 7: 838-842.

Gervais A, Hammel Y A, Pelloux S, Lepage P, Baer G., Carte N, Sorokine O, Strub J M, Koerner R, Leize E, and Van Dorsselaer A (2003) Glycosylation of human recombinant gonadotrophins: characterization and batch-to-batch consistency. Glycobiology 13 3:179-189.

Goldman M H, James D. C., Rendall M., Ison A. P., Hoare M., and Bull A. T. (1998) Monitoring recombinant human interferon-gamma N-glycosylation during perfused fluidized-bed and stirred-tank batch culture of CHO cells. Biotech.Bioeng. 60 5: 596-607.

Goochee C. F., Gramer M. J., Andersen D. C., Bahr J. B., and Rasmussen J. R. (1991) The oligosaccharides of glycoproteins: bioprocess factors affecting oligosaccharide structure and their effect on glycoprotein properties. Biotechnology (N.Y.) 9 12: 1347-1355.

Goochee C. F. and Monica T. (1990) Environmental effects on protein glycosylation. Biotechnology (N.Y.) 8 5: 421-427.

Grantham et al. (1974) Amino acid difference formula to help explain protein evolution. Science, Vol. 185, pp. 862-864

Harvey (2001) Identification of protein-bound carbohydrates by mass spectrometry. Proteomics 1, 311-238

Hayter P. M., Curling E. M. A., Gould M. L., Baines A. J., Jenkins N., Salmon I., Strange P. G., and Bull A. T. (1993) The effect of the dilution rate on CHO cell physiology and recombinant interferon-gamma production in glucose-limited chemostat culture. Biotechnology and Bioengineering 42 9: 1077-1085.

Hermentin P, Witzel R, Kanzy EJ, Diderrich G, Hoffmann D, Metzner H, Vorlop J, Haupt H. The hypothetical N-glycan charge: a number that characterizes protein glycosylation. Glycobiology. 1996 March;6(2):217-30.

Hooker A D, Goldman M H, Markham N., James D. C., Ison A. P., Bull A. T., Strange P. G., Salmon I., Baines A. J., and Jenkins N (1995) N-Glycans of recombinant human interferon-g change during batch culture of chinese hamster ovary cells. Biotech.Bioeng. 48: 639-648.

Hu W.-S. and Aunins J. G. (1997) Large-scale mammalian cell culture. Current Opinion in Biotechnology 8:148-153.

Jenkins N., Parekh R. B, and James D. C. (1996) Getting the glycosylation right: Implications for the biotechnology industry. Nature Biotechnology 14: 975-981.

Kadouri A. and Spier R. E. (1997) Some myths and messages concerning the batch and continuous culture of animal cells. Cytotechnology 24:89-98.

Kim S H, Eisenstein M, Reznikov L, Fantuzzi G, Novick D, Rubinstein M, Dinarello C A. Structural requirements of six naturally occurring isoforms of the IL-18 binding protein to inhibit IL-18. Proc Natl Acad Sci USA 2000;97: 1190-1195.

Kyung Yun-Seung, Peshwa Madhusudan V., Gryte David M., and Hu Wei-Shou (1994) High density culture of mammalian cells with dynamic perfusion based on on-line oxygen uptake rate measurements. Cytotechnology 14:183-190.

Novick, D, Kim, S-H, Fantuzzi, G, Reznikov, L, Dinarello, C, and Rubinstein, M (1999). Immunity 10, 127-136

Oh D. J., Choi S. K., and Chang H. N. (1994) High-density continuous cultures of hybridoma cells in a depth filter perfusion system. Biotechnology and Bioengineering 44:895-901.

Pearson (1990) Rapid and sensitive sequence comparison with FASTP and FASTA Methods Enzymol. 1990;183:63-98

Puren et al. (1999) Gene expression, synthesis, and secretion of interleukin 18 and interleukin 1beta are differentially regulated in human blood mononuclear cells and mouse spleen cells. Proc Natl Acad Sci USA. 96(5):2256-61.

Racher A. J. and Griffiths J. B. (1993) Investigation of parameters affecting a fixed bed bioreactor process for recombinant cell lines. Cytotechnology 13: 125-131.

Racher A. J., Looby D., and Griffiths J. B. (1993) Influence of ammonium ion and glucose on mAb production in suspension and fixed bed hybridoma cultures. Journal of Biotechnology 29: 145-156.

Sugiura T. and Kakuzaki M. (1998) Dynamics of recombinant protein production by mammalian cells in immobilized perfusion culture. Enzyme and Microbial Technology 22: 699-704.

Vigers et al., Nature. Mar. 13, 1997;386(6621):190-4.

Wang M-D., Yang M., and Butler M. (2002) Erythropoietin production from CHO cells grown by continuous culture in a fluidized-bed bioreactor. Biotechnology and Bioengineering 77 2: 194-203.

The invention claimed is:

1. A process for producing recombinant Interleukin-18 binding protein (IL-18BP) in mammalian cells comprising a cell propagation phase at about 37° C. and a production phase at a temperature ranging from about 29° C. to about 34° C. in a bioreactor under serum-free culture conditions.

2. The process according to claim 1, wherein the process is a perfusion process comprising:
 a) a cell propagation phase at 37° C. at a given perfusion rate;
 b) a production phase I at 33.5° C. at a perfusion rate that ranges from about 85 to about 65% of the given perfusion rate of step (a); and
 c) a production phase II at 32.5° C. at a perfusion rate that ranges from about 85 to about 65% of the given perfusion rate of step (a).

3. The process according to claim 2, wherein the perfusion rate of step (a) has a dilution rate in the range of about 2 to about 3 vvd.

4. The process according to claim 2, wherein the cells are associated to carriers, and production phase I of step (b) is started at a glucose consumption rate of about 250 to 350 g of Glucose per kilogram of carrier.

5. The process according to claim 1, wherein the mammalian cells are Chinese Hamster Ovary (CHO) cells.

6. The process according to claim 1, further comprising the step of collecting the cell culture supernatant.

7. The process according to claim 1, further comprising the step of purifying IL-18BP.

8. The process according to claim 6, further comprising the step of purifying IL-18BP.

9. The process according to claim 8, further comprising the step of formulating the IL-18BP into a pharmaceutical composition.

10. The process according to claim 7, further comprising the step of formulating the IL-18BP into a pharmaceutical composition.

11. The process according to claim 1, wherein the process is a fed-batch process comprising the steps of:
  a) a cell propagation phase at 37° C.; and
  b) a production phase at 29° C.

12. The process according to claim 11, wherein the total cell density in the production phase ranges between 4 to $8 \times 10^6$ cells per ml per day over at least 10 days of cell culture.

13. The process according to claim 11, wherein the viability ranges between 100 and 80% over at least 10 days of cell culture.

14. The process according to claim 11, wherein the protein productivity is higher than about 150 mg.

15. The process according to claim 11, wherein the mammalian cells are Chinese Hamster Ovary (CHO) cells.

16. The process according to claim 11, further comprising the step of collecting the cell culture supernatant.

17. The process according to claim 16, further comprising the step of purifying IL-18BP.

18. The process according to claim 17, further comprising the step of formulating the IL-18BP into a pharmaceutical composition.

19. The process according to claim 11, further comprising the step of purifying IL-18BP.

20. The process according to claim 19, further comprising the step of formulating the IL-18BP into a pharmaceutical composition.

21. The process according to claim 11, further comprising culturing cells at a temperature of 33° C. between said propagation phase and said production phase.

22. The process according to claim 1, wherein said process comprises culturing mammalian cells expressing recombinant Interleukin-18 binding protein (IL-18BP) in a bioreactor, said culturing comprising a cell propagation phase at about 37° C. and a production phase at a temperature ranging from about 29° C. to about 34° C. under serum-free culture conditions.

* * * * *

UNITED STATES PATENT AND TRADEMARK OFFICE
CERTIFICATE OF CORRECTION

PATENT NO. : 7,691,611 B2  
APPLICATION NO. : 11/915453  
DATED : April 6, 2010  
INVENTOR(S) : Urs Weber and Thierry Ziegler It is certified that error appears in the above-identified patent and that said Letters Patent is hereby corrected as shown below:

Column 2,  
Line 12, "It also it has the advantage to define" should read  
--It also has the advantage of defining--.

Column 6,  
Lines 7-8, "rate that that ranges" should read --rate that ranges--.  
Line 35, "allow controlling" should read --allow for controlling--.

Column 7,  
Line 35, "such as, e.g., e.g.," should read --such as, e.g.,--.

Column 8,  
Line 2, "comprises a step" should read --comprise a step--.

Column 9,  
Line 3, "IL18BP" should read --IL-18BP--.  
Line 28, "term "IL-18PB", as" should read --term "IL-18BP", as--.

Column 13,  
Line 65, "formation or dimers" should read --formation of dimers--.

Column 17,  
Line 30, "Fibra-Cele" should read --Fibra-Cel®--.  
Line 35, "Fibra-Cele" should read --Fibra-Cel®--.  
Line 54, "IL18BP" should read --IL-18BP--.

Column 19,  
Line 32, "(100%)" should read --(~100%)--.

Signed and Sealed this

First Day of June, 2010

David J. Kappos  
*Director of the United States Patent and Trademark Office*

Column 25,
Line 58, "Isoform Classification Due the" should read
--Isoform Classification
Due to the--.